United States Patent
Nagata et al.

(10) Patent No.: US 11,072,707 B2
(45) Date of Patent: Jul. 27, 2021

(54) RESIN MATERIAL FOR ACOUSTIC WAVE PROBE, ACOUSTIC LENS, ACOUSTIC WAVE PROBE, ACOUSTIC WAVE MEASUREMENT APPARATUS, ULTRASONIC DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yuzo Nagata, Kanagawa (JP); Yoshihiro Nakai, Kanagawa (JP); Toshihide Yoshitani, Kanagawa (JP); Shigeki Uehira, Kanagawa (JP); Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 76 days.

(21) Appl. No.: 16/364,899

(22) Filed: Mar. 26, 2019

(65) Prior Publication Data
US 2019/0218394 A1 Jul. 18, 2019

Related U.S. Application Data

(63) Continuation of application No. PCT/JP2017/034168, filed on Sep. 21, 2017.

(30) Foreign Application Priority Data
Sep. 27, 2016 (JP) .............................. JP2016-188531

(51) Int. Cl.
| | | |
|---|---|---|
| C08L 83/04 | (2006.01) | |
| C08F 265/06 | (2006.01) | |
| C08F 265/10 | (2006.01) | |
| C08G 77/20 | (2006.01) | |
| C08G 77/442 | (2006.01) | |
| C08F 257/02 | (2006.01) | |
| A61B 8/00 | (2006.01) | |
| C08L 83/10 | (2006.01) | |
| H04R 1/34 | (2006.01) | |
| C08F 290/06 | (2006.01) | |
| C08F 293/00 | (2006.01) | |
| H04R 17/00 | (2006.01) | |
| H04R 19/00 | (2006.01) | |
| A61B 8/12 | (2006.01) | |
| G10K 11/30 | (2006.01) | |

(52) U.S. Cl.
CPC ............ *C08L 83/04* (2013.01); *A61B 8/00* (2013.01); *A61B 8/4281* (2013.01); *A61B 8/445* (2013.01); *C08F 257/02* (2013.01); *C08F 265/06* (2013.01); *C08F 265/10* (2013.01); *C08F 290/06* (2013.01); *C08F 293/00* (2013.01); *C08L 83/10* (2013.01); *H04R 1/34* (2013.01); *H04R 17/00* (2013.01); *H04R 19/00* (2013.01); *A61B 8/12* (2013.01); *C08G 77/20* (2013.01); *C08G 77/442* (2013.01); *G10K 11/30* (2013.01)

(58) Field of Classification Search
CPC ...... C08L 83/10; C08G 77/442; A61B 8/4281
See application file for complete search history.

(56) References Cited

U.S. PATENT DOCUMENTS

| | | | |
|---|---|---|---|
| 4,901,729 A | 2/1990 | Saitoh et al. | |
| 5,050,128 A | 9/1991 | Saitoh et al. | |
| 5,505,205 A | 4/1996 | Solomon et al. | |
| 2002/0183473 A1* | 12/2002 | Matyjaszewski | C08F 293/00 526/335 |
| 2004/0054115 A1* | 3/2004 | Lautenschlager | C08G 77/38 528/25 |
| 2004/0120982 A1* | 6/2004 | Diana | G02B 1/043 424/429 |
| 2006/0070801 A1 | 4/2006 | Parker et al. | |
| 2010/0137517 A1* | 6/2010 | Kennedy | C08G 77/442 525/94 |
| 2011/0143095 A1 | 6/2011 | Tada et al. | |
| 2011/0319768 A1* | 12/2011 | Saito | A61B 8/4281 600/472 |
| 2015/0232701 A1* | 8/2015 | Aoki | C09D 183/10 359/296 |

(Continued)

FOREIGN PATENT DOCUMENTS

| | | |
|---|---|---|
| JP | 62-233149 A | 10/1987 |
| JP | 63-220847 A | 9/1988 |

(Continued)

OTHER PUBLICATIONS

Notice of Reasons for Refusal dated Oct. 15, 2019 issued by the Japanese Patent Office in corresponding Application No. 2018-542492.
Communication dated Nov. 7, 2019 from the European Patent Office in application No. 17855945.6.
International Search Report dated Dec. 12, 2017 from the International Searching Authority in counterpart International Application No. PCT/JP2017/034168.

(Continued)

*Primary Examiner* — Jeffrey C Mullis
(74) *Attorney, Agent, or Firm* — Sughrue Mion, PLLC

(57) ABSTRACT

Provided are a resin material for an acoustic wave probe which contains a polymer formed of at least one of a structural unit (a) having a specific polysiloxane bond or a structural unit (b) having a specific partial structure, in which the structural unit (b) having the specific partial structure is an acryloyloxy structural unit (b1), an acrylamide structural unit (b2), or a styrene structural unit (b3); an acoustic lens; an acoustic wave probe; an acoustic wave measurement apparatus; an ultrasound diagnostic apparatus; a photoacoustic wave measurement apparatus; and an ultrasound endoscope.

21 Claims, 1 Drawing Sheet

(56) References Cited

U.S. PATENT DOCUMENTS

2016/0051228 A1    2/2016  Nakai et al.

FOREIGN PATENT DOCUMENTS

| | | |
|---|---|---|
| JP | 08-615 A | 1/1996 |
| JP | 8-103443 A | 4/1996 |
| JP | 8-305375 A | 11/1996 |
| JP | 2011-182223 A | 9/2011 |
| JP | 2016-108396 A | 6/2016 |
| WO | 2010/024117 A1 | 3/2010 |
| WO | 2011/133408 A2 | 10/2011 |
| WO | 2016/088699 A1 | 6/2016 |

OTHER PUBLICATIONS

International Preliminary Report on Patentability dated Apr. 2, 2019 with translation of the Written Opinion dated Dec. 12, 2017 from the International Bureau in counterpart with International Application No. PCT/JP2017/034168.
Written Opinion dated Dec. 12, 2017 from the International Bureau in counterpart International Application No. PCT/JP2017/034168.
Communication dated Aug. 23, 2019, from the European Patent Office in corresponding European Application No. 17855945.6.

* cited by examiner

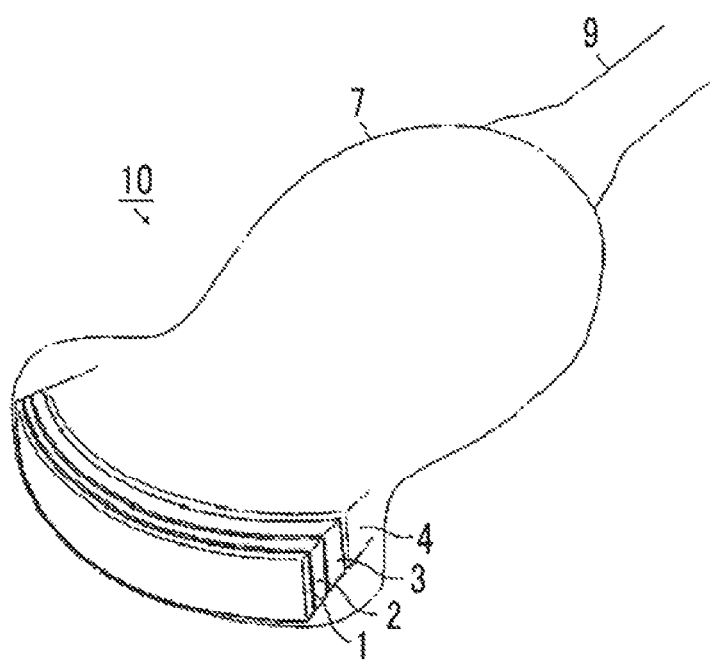

RESIN MATERIAL FOR ACOUSTIC WAVE PROBE, ACOUSTIC LENS, ACOUSTIC WAVE PROBE, ACOUSTIC WAVE MEASUREMENT APPARATUS, ULTRASONIC DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2017/034168 filed on Sep. 21, 2017, which claims priority under 35 U.S.C. § 119 (a) to Japanese Patent Application No. 2016-188531 filed in Japan on Sep. 27, 2016. Each of the above applications is hereby expressly incorporated by reference, in its entirety, into the present application.

BACKGROUND OF THE INVENTION

1. Field of the Invention

The present invention relates to a resin material for an acoustic wave probe, and an acoustic lens and acoustic wave probe. Furthermore, the present invention relates to an acoustic wave measurement apparatus, an ultrasound diagnostic apparatus, a photoacoustic wave measurement apparatus, and an ultrasound endoscope.

2. Description of the Related Art

In an acoustic wave measurement apparatus, an acoustic wave probe is used which irradiates a test object or a site (hereinafter, simply referred to as a subject) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, an ultrasound diagnostic apparatus transmits an ultrasonic wave to the interior of a test object, receives the ultrasonic wave reflected by the tissues inside the test object, and displays the received ultrasonic wave as an image. A photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

An acoustic wave measurement apparatus performs transmission and reception of an acoustic wave on a living body (typically a human body) which is a test object. Therefore, it is necessary to fulfill requirements such as consistency in the acoustic impedance within the living body and a decrease in acoustic attenuation.

For example, a probe for an ultrasound diagnostic apparatus (also referred to as an ultrasound probe) which is a kind of acoustic wave probe comprises a piezoelectric element which transmits and receives an ultrasonic wave and an acoustic lens which is a portion coming into contact with a living body. An ultrasonic wave oscillating from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body. Therefore, the ultrasonic wave is not efficiently incident on the living body. For this reason, it is difficult to obtain a favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance of a living body (in the case of a human body, $1.4 \times 10^6$ to $1.7 \times 10^6$ kg/m²/sec) and which has a low ultrasonic attenuation is used as a material of the acoustic lens. For example, JP1996-010344A (JP-H08-010344A) discloses that an ultrasonic lens of a medical ultrasonic transducer assembly is manufactured from a flexible material having a low acoustic velocity such as silicone rubber.

SUMMARY OF THE INVENTION

A resin made of silicone has a low mechanical strength (for example, hardness). For this reason, in the medical ultrasonic transducer assembly of JP1996-010344A (JP-H08-010344A), a polymer having a predetermined hardness, which is obtained by polymerizing tris(trimethylsiloxy)methacryloxypropylsilane, bis(methacryl oxypropyl) tetrakis(trimethyl siloxy)disiloxane, and methyl methacrylate has been used as a protective cover for the ultrasonic lens. JP1996-010344A (JP-H08-010344A) discloses that an acoustic velocity and impedance of this polymer substantially correspond to those of soft tissues of a human body. However, it was found based on the study of the inventors of the present invention that the protective cover made of the polymer disclosed in JP1996-010344A (JP-H08-010344A) has a large acoustic attenuation. Accordingly, in the above-described assembly disclosed in JP1996-010344A (JP-H08-010344A), it is necessary to reduce the acoustic attenuation in interface means including the protective cover and the ultrasonic lens, which transmits ultrasonic energy received from a subject to the transducer.

In view of the above circumstances, an object of the present invention is to provide a resin material suitable as a lens of an acoustic wave probe, which realizes an acoustic impedance close to that of a living body value by being molded to reduce acoustic attenuation even at high frequencies (for example, 10 MHz and 15 MHz), thereby capable of obtaining a resin article having excellent hardness.

In addition, another object of the present invention is to provide an acoustic lens using the above-described resin material for an acoustic wave probe as a constituent material, an acoustic wave probe, an acoustic wave measurement apparatus, an ultrasound diagnostic apparatus, a photoacoustic wave measurement apparatus, and an ultrasound endoscope.

In addition, still another object of the present invention is to provide an acoustic lens that has an acoustic impedance value close to that of a living body, is capable of effectively suppressing the acoustic attenuation even at high frequencies, and has a desired acoustic velocity; and an acoustic wave probe, an acoustic wave measurement apparatus, an ultrasound diagnostic apparatus, a photoacoustic wave measurement apparatus, and an ultrasound endoscope, which have this acoustic lens.

The above-described objects are achieved by the following means.

<1> A resin material for an acoustic wave probe, comprising a polymer that is formed of at least one of a structural unit (a) having a polysiloxane bond represented by Formula (1) or a structural unit (b) having a partial structure represented by Formula (2), in which the structural unit (b) having the partial structure represented by Formula (2) is an acryloyloxy structural unit (b1), an acrylamide structural unit (b2), or a styrene structural unit (b3).

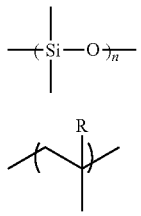

Formula (1)

Formula (2)

In the formulas, n represents an integer of 3 or more, and R represents a hydrogen atom or a monovalent organic group; and a bond line extending downward from a carbon atom to which R bonds represents a bond.

<2> The resin material for an acoustic wave probe according to <1>, in which the polymer is a graft polymer having the polysiloxane bond represented by Formula (1) at a side chain.

<3> The resin material for an acoustic wave probe according to <1> or <2>, in which the structural unit having the polysiloxane bond represented by Formula (1) is represented by Formula (3), and the acryloyloxy structural unit (b1) is represented by Formula (4), the acrylamide structural unit (b2) is represented by Formula (5), and the styrene structural unit (b3) is represented by Formula (6).

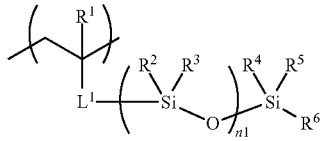

Formula (3)

In the formula, $R^1$ to $R^6$ each independently represent a hydrogen atom or a monovalent organic group, $L^1$ represents a divalent linking group, and n1 represents an integer of 3 to 10,000.

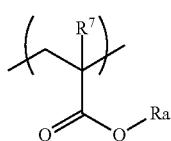

Formula (4)

In the formula, $R^7$ and Ra each independently represent a hydrogen atom or a monovalent organic group.

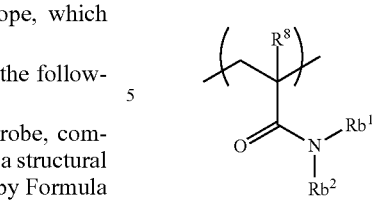

Formula (5)

In the formula, $R^8$, $Rb^1$, and $Rb^2$ each independently represent a hydrogen atom or a monovalent organic group.

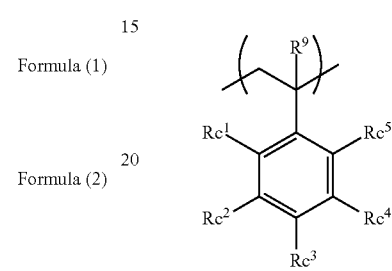

Formula (6)

In the formula, $R^9$ and $Rc^1$ to $Rc^5$ each independently represent a hydrogen atom or a monovalent organic group.

<4> The resin material for an acoustic wave probe according to <1>, in which the polymer is a block polymer having at least one of a block formed of the structural unit (a) having the polysiloxane bond represented by Formula (1) or a block formed of the structural unit (b) having the partial structure represented by Formula (2).

<5> The resin material for an acoustic wave probe according to <4>, in which the structural unit (a) having the polysiloxane bond represented by Formula (1) is represented by Formula (7), and the structural unit (b) having the partial structure represented by Formula (2) is represented by Formula (6).

Formula (7)

In the formula, $R^{10}$ and $R^{11}$ each independently represent a hydrogen atom or a monovalent organic group, $L^2$ and $L^3$ each independently represent a divalent linking group, and m represents an integer of 3 to 10,000.

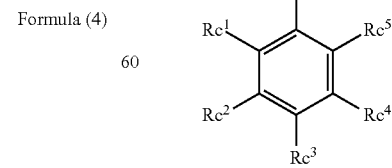

Formula (6)

In the formula, $R^9$ and $Rc^1$ to $Rc^5$ each independently represent a hydrogen atom or a monovalent organic group.

<6> The resin material for an acoustic wave probe according to <4>, in which the structural unit (a) having the polysiloxane bond represented by Formula (1) is represented by Formula (7), and the structural unit (b) having the partial structure represented by Formula (2) is represented by Formula (4).

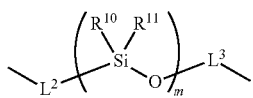

Formula (7)

In the formula, $R^{10}$ and $R^{11}$ each independently represent a hydrogen atom or a monovalent organic group, $L^2$ and $L^3$ each independently represent a divalent linking group, and m represents an integer of 3 to 10,000.

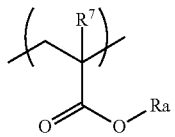

Formula (4)

In the formula, $R^7$ and Ra each independently represent a hydrogen atom or a monovalent organic group.

<7> The resin material for an acoustic wave probe according to any one of <1> to <6>, in which, in the polymer, a mass average molecular weight of the structural unit having the polysiloxane bond represented by Formula (1) is 4,000 or more.

<8> The resin material for an acoustic wave probe according to any one of <1> to <4>, in which the structural unit (b) having the partial structure represented by Formula (2) is the styrene structural unit (b3).

<9> The resin material for an acoustic wave probe according to any one of <1> to <4>, in which the structural unit (b) having the partial structure represented by Formula (2) is the acryloyloxy structural unit (b1).

<10> The resin material for an acoustic wave probe according to any one of <1> to <9>, in which a density of the polymer is 1.05 g/cm³ or more.

<11> The resin material for an acoustic wave probe according to any one of <1> to <10>, in which the polymer contains a fluorine atom.

<12> The resin material for an acoustic wave probe according to <11>, in which the structural unit (b) having the partial structure represented by Formula (2) has 5 or more fluorine atoms.

<13> The resin material for an acoustic wave probe according to any one of <1> to <12>, in which a mass average molecular weight of the polymer is 50,000 or more.

<14> An acoustic lens comprising the resin material for an acoustic wave probe according to any one of <1> to <13>.

<15> An acoustic lens having a damping coefficient of 0.50 dB/(MHz·mm) or less at a frequency of 15 MHz, an acoustic impedance of $1.30 \times 10^6$ kg/m²/s or more and $1.70 \times 10^6$ kg/m²/s or less, and an acoustic velocity of 1300 m/s or less.

<16> The acoustic lens according to <15>, comprising a resin material for an acoustic wave probe that contains a polymer formed of at least one of a structural unit (a) having a polysiloxane bond represented by Formula (1) or a structural unit (b) having a partial structure represented by Formula (2), in which the structural unit (b) having the partial structure represented by Formula (2) is an acryloyloxy structural unit (b1), an acrylamide structural unit (b2), or a styrene structural unit (b3).

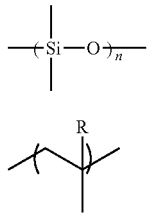

Formula (1)

Formula (2)

In the formulas, n represents an integer of 3 or more, and R represents a hydrogen atom or a monovalent organic group; and a bond line extending downward from a carbon atom to which R bonds represents a bond.

<17> An acoustic wave probe comprising the acoustic lens according to any one of <14> to <16>.

<18> An acoustic wave measurement apparatus comprising the acoustic wave probe according to <17>.

<19> An ultrasound diagnostic apparatus comprising the acoustic wave probe according to <17>.

<20> A photoacoustic wave measurement apparatus comprising the acoustic lens according to any one of <14> to <16>.

<21> An ultrasound endoscope comprising the acoustic lens according to any one of <14> to <16>.

Unless otherwise specified in the description of the present specification, in a case where there are groups having a plurality of the same reference numerals as each other in general formulae representing compounds, these may be the same as or different from each other, and a group (for example, an alkyl group) specified by each group may further have a substituent. In addition, the "Si—H group" means a group having three bonds in addition to —H on a silicon atom, but the description of the bonds is not repeated and the notation is simplified.

In the present specification, a case of referring to "acryl" broadly refers to a group of structures having an acryloyl group, and includes a structure having a substituent (for example, an alkyl group) at an α-position.

In addition, in the present specification, "to" means a range including numerical values denoted before and after "to" as a lower limit value and an upper limit value.

Unless otherwise specified, a mass average molecular weight in the present specification refers to a value (in terms of polystyrene) measured through gel permeation chromatography (GPC).

In particular, the mass average molecular weight can be measured using Tetrahydrofuran (manufactured by FUJIFILM Wako Pure Chemical Corporation) as an eluent, TSKgel (registered trademark) G3000HXL+TSKgel (registered trademark) G2000HXL as columns, and a RI detector under the conditions of a temperature of 23° C. and a flow rate of 1 mL/min after preparing a GPC apparatus HLC-8220 (manufactured by TOSOH CORPORATION).

The resin material for an acoustic wave probe of the present invention is molded, thereby capable of realizing acoustic impedance close to that of a living body, or decreasing acoustic attenuation even at higher frequencies so as to provide a resin article in which improvement in hardness is realized. Accordingly, it is possible to provide the acoustic lens, the acoustic wave probe, the acoustic wave measurement apparatus, the ultrasound diagnostic apparatus, the photoacoustic wave measurement apparatus, and the ultrasound endoscope, which are excellent in transmission and reception performance of acoustic wave and also excellent in mechanical characteristics.

Furthermore, the acoustic lens, the acoustic wave probe, the acoustic wave measurement apparatus, the ultrasound diagnostic apparatus, the photoacoustic wave measurement apparatus, and the ultrasound endoscope of the present invention have a member formed by using the resin material for an acoustic wave probe of the present invention, in which the acoustic impedance value is close to that of a living body, or the acoustic attenuation can be effectively suppressed, and therefore the mechanical strength is also excellent.

The acoustic wave probe, the acoustic wave measurement apparatus, the ultrasound diagnostic apparatus, the photoacoustic wave measurement apparatus, and the ultrasound endoscope of the present invention have the above-described acoustic lens, and thus are excellent in the transmission and reception performance of the acoustic wave. Therefore, favorable images can be obtained particularly in the ultrasound diagnostic apparatus, the photoacoustic wave measurement apparatus, and the ultrasound endoscope.

BRIEF DESCRIPTION OF THE DRAWING

The FIGURE is a perspective transparent view of an example of a convex ultrasound probe which is an embodiment of an acoustic wave probe.

DESCRIPTION OF THE PREFERRED EMBODIMENTS

<<Resin Material for Acoustic Wave Probe>>

A resin material for an acoustic wave probe of the embodiment of the present invention (hereinafter simply referred to as a resin material, moreover abbreviated as a resin) contains a polymer (hereinafter referred to as "specific polymer") that is formed of at least one of a structural unit having a polysiloxane bond represented by Formula (1) or a structural unit having a partial structure represented by Formula (2). The structural unit having the partial structure represented by Formula (2) is an acryloyloxy structural unit (b1), an acrylamide structural unit (b2), or a styrene structural unit (b3).

A specific structure of this specific polymer is not particularly limited, and examples thereof include a random polymer, a block polymer, a graft polymer, and the like.

The resin material for an acoustic wave probe of the embodiment of the present invention may be in a form in which the resin material is made of a specific polymer or may be in a form in which, in addition to the specific polymer, organosiloxane such as vinylsilicone and hydrosilicone to be described later; additives in common use such as fillers, catalysts, solvents, dispersants, pigments, dyes, antistatic agents, flame retardants, and heat conductivity improvers; and optional components exhibiting additional actions are formulated. In addition, in a case where the resin material for an acoustic wave probe of the embodiment of the present invention is composed of two or more components, a form of a composition in which each component is homogeneously mixed is preferable.

The resin material for an acoustic wave probe of the embodiment of the present invention may be in a form having fluidity by being mixed with a solvent or the like, or may be in a form of pellets formed into a predetermined shape.

Hereinafter, a structural unit (a) having a polysiloxane bond represented by Formula (1) will be simply referred to as "structural unit (a)". In addition, a structural unit (b) having a partial structure represented by Formula (2) will be simply referred to as "structural unit (b)". Furthermore, the acryloyloxy structural unit (b1) will be simply referred to as a "structural unit (b1)". Furthermore, the acrylamide structural unit (b2) will be simply referred to as a "structural unit (b2)". Furthermore, the styrene structural unit (b3) will be simply referred to as a "structural unit (b3)".

By molding the resin material for an acoustic wave probe of the embodiment of the present invention, the resin material becomes excellent in any characteristics of an acoustic impedance value close to that of a living body, a decrease in acoustic attenuation (particularly acoustic attenuation at high frequencies), and excellent hardness, and thus can be suitably used as a constituent material of members constituting the acoustic wave probe. Action and mechanism thereof are not certain yet, are considered to be as follows.

In a case of a simple silicone resin, a reduction in the acoustic attenuation is favorable, but hardness was low. It is considered that this low hardness is due to a condition that a resin does not have a filler or a high-hardness structure. On the other hand, it is considered that, in the specific polymer used in the present invention, a hard segment is introduced into the polymer, thereby improving the hardness of the obtained resin. That is, it is possible to achieve both a reduction in the acoustic attenuation and a high level of the hardness. Moreover, in the specific polymer used in the present invention, structures and elements having a high specific gravity can be introduced into the hard segment of the polymer. For this reason, it is considered that an acoustic impedance value of a resin sheet obtained by processing the resin material for an acoustic wave probe of the embodiment of the present invention can be close to that of the living body.

Therefore, even in a case where the resin material for an acoustic wave probe of the embodiment of the present invention does not contain an inorganic filler, it is possible to produce a resin sheet exhibiting the excellent characteristics described above.

(Structural Unit (a) Having Polysiloxane Bond Represented by Formula (1))

Formula (1)

n represents an integer of 3 or more. A bond line extending downward from a silicon atom represents a bond.

n is preferably an integer of 3 to 10,000, more preferably an integer of 10 to 500, and particularly preferably an integer of 50 to 300. In a case where n is within the above-described range, mobility to acoustic waves is low, or compatibility with hard segments is also high, and therefore phase separation can be suppressed, and a reduction in acoustic attenuation is favorable.

Since the specific polymer used in the present invention has high compatibility with the structure of Formula (2), and therefore phase separation is suppressed, and the reduction in the acoustic attenuation is favorable, the specific polymer is preferably a graft polymer having the polysiloxane bond represented by Formula (1) at a side chain.

In the specific polymer used in the present invention, the structural unit (a) is preferably a structural unit represented by Formula (3).

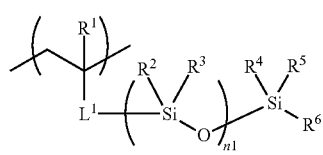

Formula (3)

In the formula, $R^1$ to $R^6$ each independently represent a hydrogen atom or a monovalent organic group, $L^1$ represents a divalent linking group, and n1 represents an integer of 3 to 10,000.

Examples of the monovalent organic group represented by $R^1$ to $R^6$ include an alkyl group, a cycloalkyl group, an alkenyl group, an aryl group, a heteroaryl group, an alkoxy group, an aryloxy group, a heteroaryloxy group, an alkylthio group, an arylthio group, a heteroarylthio group, an alkylamino group, an arylamino group, a heteroarylamino group, an alkyloxycarbonyl group, an aryloxycarbonyl group, a heteroaryloxycarbonyl group, an alkylaminocarbonyl group, an arylaminocarbonyl group, a heteroarylaminocarbonyl group, and a halogen group, and any of an alkyl group, a cycloalkyl group, an alkenyl group, and an aryl group is preferable. Hereinafter, details will be described.

The number of carbon atoms in an alkyl group is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group is preferably 3 to 10, more preferably 5 to 10, and even more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group is preferably 2 to 10, more preferably 2 to 4, and even more preferably 2. Examples of the alkenyl group include a vinyl group, an allyl group, and a butenyl group.

The number of carbon atoms in an aryl group is preferably 6 to 12, more preferably 6 to 10, and even more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom (for example, a fluorine atom, a chlorine atom, a bromine atom, and an iodine atom), an alkyl group, a cycloalkyl group, an alkenyl group, an aryl group, an alkoxy group, an aryloxy group, an alkylthio group, an arylthio group, a silyl group, and a cyano group.

Examples of the group having a substituent include an alkyl fluoride group.

$R^1$ to $R^6$ are preferably an alkyl group, an alkenyl group, or an aryl group, and more preferably an alkyl group having 1 to 4 carbon atoms, $R^1$ to $R^5$ are particularly preferably a methyl group from the viewpoint of reducing acoustic attenuation, and $R^6$ is preferably a butyl group.

The divalent linking group in $L^1$ is not particularly limited as long the effect of the present invention is exerted thereby. Examples thereof include a single bond; an alkylene group (the number of carbon atoms is preferably from 1 to 12, more preferably from 1 to 8, even more preferably from 1 to 6, and particularly preferably from 1 to 3. Specific examples thereof include methylene, ethylene, n-propylene, isopropylene, n-butylene, t-butylene, and n-octylene); an arylene group (the number of carbon atoms is preferably from 6 to 18, more preferably from 6 to 14, and particularly preferably from 6 to 12. Specific examples thereof include phenylene, tolylene, and naphthylene); an oxyalkylene group (the number of carbon atoms is preferably from 1 to 12, more preferably from 1 to 8, even more preferably from 1 to 6, and particularly preferably from 1 to 3. Specific examples thereof include oxymethylene, oxyethylene, oxypropylene, and oxydimethyl ethylene); an oxyarylene group (the number of carbon atoms is preferably from 6 to 18, more preferably from 6 to 14, and particularly preferably from 6 to 12. Specific examples thereof include oxyphenylene, oxytolylene (divalent toluene), and oxynaphthylene); and the like, among which an alkylene group and an oxyalkylene group are preferable.

The oxyalkylene group and the oxyarylene group may be bonded to adjacent Si at any side, but it is preferable that the alkylene group of the oxyalkylene group and the arylene group of the oxyarylene group are bonded to adjacent Si. A methylene group and a phenylene group are more preferable.

n1 is synonymous with the preferred range of n described above.

(Structural Unit (b) Having the Partial Structure Represented by Formula (2))

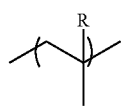

Formula (2)

In the formula, R represents a hydrogen atom or a monovalent organic group. A bond line extending downward from a carbon atom to which R bonds represents a bond.

(Acryloyloxy Structural Unit (b1))

In the specific polymer used in the present invention, the structural unit (b1) is preferably a structural unit represented by Formula (4).

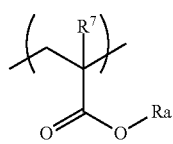

Formula (4)

In the formula, $R^7$ and Ra each independently represent a hydrogen atom or a monovalent organic group.

Examples of the monovalent organic group represented by $R^7$ include a monovalent organic group represented by $R^1$ in Formula (3).

$R^7$ is preferably a hydrogen atom or an alkyl group, and the number of carbon atoms in an alkyl group is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

Specific examples of the monovalent organic group represented by Ra include a monovalent organic group represented by $R^1$ in Formula (3).

Ra is preferably a hydrogen atom, an alkyl group, or an aryl group.

The number of carbon atoms in the alkyl group is preferably 1 to 10, and more preferably 1 to 6. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in an aryl group is preferably 6 to 12, more preferably 6 to 10, even more preferably 6 to 8, and particularly preferably 6. Examples of the aryl group include a phenyl group, a tolyl group, and a naphthyl group.

The monovalent organic group represented by $R^7$ and Ra may have a substituent. Examples of such a substituent include a halogen atom (for example, a fluorine atom, a chlorine atom, a bromine atom, and an iodine atom), an alkyl group, a cycloalkyl group, an alkenyl group, an aryl group, an alkoxy group, an aryloxy group, an alkylthio group, an arylthio group, a silyl group, and a cyano group.

From the viewpoint of reduction in the acoustic attenuation and realization of the acoustic impedance value close to that of the living body, a halogen atom is preferable, and among them, a fluorine atom is more preferable.

Examples of the group having a substituent include an alkyl group having a fluorine atom and an aryl group having a fluorine atom.

(Acrylamide Structural Unit (b2))

In the specific polymer used in the present invention, the structural unit (b2) is preferably a structural unit represented by Formula (5).

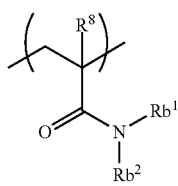

Formula (5)

In the formula, $R^8$, $Rb^1$, and $Rb^2$ each independently represent a hydrogen atom or a monovalent organic group.

Specific examples of the monovalent organic group represented by $R^8$ include a monovalent organic group represented by $R^1$ in Formula (3).

$R^8$ is preferably a hydrogen atom or an alkyl group, and more preferably an alkyl group. The number of carbon atoms in an alkyl group is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

Specific examples of the monovalent organic group represented by $Rb^1$ and $Rb^2$ include a monovalent organic group represented by $R^1$ in Formula (3).

$Rb^1$ and $Rb^2$ are preferably a hydrogen atom or an aryl group.

The number of carbon atoms in an aryl group is preferably 6 to 12, more preferably 6 to 10, even more preferably 6 to 8, and particularly preferably 6. Examples of the aryl group include a phenyl group, a tolyl group, and a naphthyl group.

The monovalent organic group represented by $R^8$, $Rb^1$, and $Rb^2$ may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include an alkyl group having a fluorine atom and a perfluoroaryl group.

(Styrene Structural Unit (b3))

In the specific polymer used in the present invention, the structural unit (b3) is preferably a structural unit represented by Formula (6).

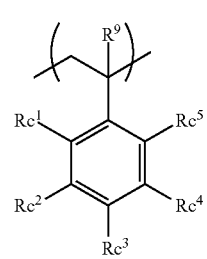

Formula (6)

In the formula, $R^9$ and $Rc^1$ to $Rc^5$ each independently represent a hydrogen atom or a monovalent organic group.

Specific examples of the monovalent organic group represented by $R^9$ include a monovalent organic group represented by $R^1$ in Formula (3). $R^9$ is preferably a hydrogen atom.

Specific examples of the monovalent organic group represented by $Rc^1$ to $Rc^5$ include a monovalent organic group represented by $R^1$ in Formula (3) and a halogen atom.

$Rc^1$ to $Rc^5$ are preferably a hydrogen atom, an alkyl group, or a halogen atom.

The number of carbon atoms in an alkyl group is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

As a halogen atom, a fluorine atom or a bromine atom is preferable, and a fluorine atom is more preferable.

The monovalent organic group represented by $R^9$ and $Rc^1$ to $Rc^5$ may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include an alkyl group having a fluorine atom and an aryl group having a fluorine atom.

In the specific polymer used in the present invention, it is preferable that the structural unit (a) is represented by Formula (3), the structural unit (b1) is represented by Formula (4), the structural unit (b2) is represented by Formula (5), and the structural unit (b3) is represented by Formula (6). The reason for this is that the specific polymer has a structure that is unlikely to respond to acoustic waves, and thus the reduction in the acoustic attenuation is favorable, and the specific polymer has a rigid structure, and thus the mechanical strength (hardness) is high.

It is preferable that the specific polymer used in the present invention is a block polymer composed of at least one of a block formed of the structural unit (a) or a block formed of the structural unit (b), so that the mobility of the whole polymer is lowered, and the mechanical strength (hardness) is high.

It is preferable that, in the block polymer, the structural unit (a) is represented by Formula (7) and the structural unit (b) is represented by Formula (6), so that the mechanical strength (hardness) is high. Furthermore, the compatibility between the structural unit represented by Formula (7) and the structural unit represented by Formula (6) is high, the phase separation is suppressed, and the reduction in the acoustic attenuation is favorable, which are preferable.

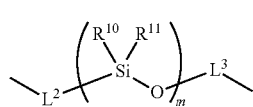

Formula (7)

In the formula, $R^{10}$ and $R^{11}$ each independently represent a hydrogen atom or a monovalent organic group, $L^2$ and $L^3$ each independently represent a divalent linking group, and m represents an integer of 3 to 10,000.

The organic group represented by $R^{10}$ and $R^{11}$ is synonymous with the monovalent organic group represented by $R^1$ in Formula (3), and the preferred range thereof is also the same.

The linking group represented by $L^2$ and $L^3$ is synonymous with the linking group represented by $L^1$ in Formula (3), and the preferred range thereof is also the same.

m is preferably an integer of 10 to 1000, and more preferably an integer of 50 to 300.

The specific polymer used in the present invention preferably has a fluorine atom, and it is particularly preferable that the structural unit (b) has a fluorine atom from the viewpoint of reducing the acoustic attenuation and increasing the acoustic impedance. In addition, in order to further increase the density, the structural unit (b) preferably has 5 or more fluorine atoms.

A content of fluorine atoms in the specific polymer is preferably from 1 to 100 mmol/g, more preferably from 2 to 50 mmol/g, and even more preferably from 3 to 20 mmol/g.

The content of fluorine atoms in the specific polymer can be calculated by analyzing a compositional ratio in the polymer by NMR.

The content of fluorine atoms in the specific polymer present in the acoustic lens and the like can also be measured by analysis methods such as NMR and elemental analysis.

Specific examples of the structural unit (b) containing fluorine atoms include the following compounds. Examples of the acryloyloxy structural unit (b1) include structural units derived from pentafluorophenyl methacrylate, 2,2,2-trifluoroethyl methacrylate, 2,2,2-trifluoropropyl methacrylate, 2,2,3,3,3-pentafluoropropyl methacrylate, 1H,1H,2H,2H-nonafluorohexyl methacrylate, 2-(perfluorobutyl)ethyl methacrylate, 3-(perfluorobutyl)-2-hydroxypropyl methacrylate, 2-(perfluorooctyl)ethyl methacrylate, 3-(perfluorooctyl)-2-hydroxypropyl methacrylate, 2-(perfluorodecyl) ethyl methacrylate, 2-(perfluoro-3-methylbutyl)ethyl methacrylate, 3-(perfluoro-3-methylbutyl)-2-hydroxypropyl methacrylate, 2-(perfluoro-5-methylhexyl)ethyl methacrylate, 3-(perfluoro-5-methylhexyl)-2-hydroxypropyl methacrylate, 2-(perfluoro-7-methyloctyl)ethyl methacrylate, 3-(perfluoro-7-methyloctyl)ethyl methacrylate, tetrafluoropropyl methacrylate, octafluoropentyl methacrylate, dodecafluoroheptyl methacrylate, hexadecafluorononyl methacrylate, 1-(trifluoromethyl)trifluoroethyl methacrylate, hexafluorobutyl methacrylate, pentafluorophenoxy methacrylate, 1,1,1,3,3,3-hexafluoroisopropyl methacrylate, pentafluorobenzyl methacrylate, methyl α-trifluoromethyl methacrylate, 2,2,2-trifluoroethyl acrylate, 2,2,3,3,3-pentafluoropropyl acrylate, 2-(perfluorobutyl)ethyl acrylate, 3-(perfluorobutyl)-2-hydroxypropyl acrylate, 2-(perfluorohexyl)ethyl acrylate, 3-(perfluorohexyl)-2-hydroxypropyl acrylate, 2-(perfluorooctyl)ethyl acrylate, 3-(perfluorooctyl)-2-hydroxypropyl acrylate, 2-(perfluorodecyl)ethyl acrylate, 2-(perfluoro-3-methylbutyl)ethyl acrylate, 3-(perfluoro-3-methoxybutyl)-2-hydroxypropyl acrylate, 2-(perfluoro-5-methylhexyl)ethyl acrylate, 3-(perfluoro-5-methylhexyl)-2-hydroxypropyl acrylate, 2-(perfluoro-7-methyloctyl)-2-hydroxypropyl acrylate, tetrafluoropropyl acrylate, octafluoropentyl acrylate, or dodecafluoroheptyl acrylate. Examples of the styrene structural unit (b3) include structural units derived from p-fluorostyrene, pentafluorostyrene, or 3,5-bis(trifluoromethyl)styrene.

In the specific polymer used in the present invention, since the structural unit (b) is an acryloyloxy structural unit, the interaction between the polymers increases due to the dipole interaction between the esters of the acryloyloxy structure, thereby increasing the hardness. In addition, by improvement in the copolymerizability with the structural unit (a), the compatibility between the structural unit (a) and the structural unit (b) is improved, and therefore the acoustic attenuation is further improved.

In the specific polymer used in the present invention, since the structural unit (b) is a styrene structural unit, a nonpolar structure is obtained, and therefore the compatibility between the structural unit (b) and the structural unit (a) having the polysiloxane bond is increased, and the reduction in the acoustic attenuation is favorable. Therefore, it is preferable that the structural unit (b) is the styrene structural unit (b3).

The structural unit (b) having the partial structure represented by Formula (2) may be used alone, two or more of the structural unit (b1), the structural unit (b2), and the structural unit (b3) may be contained in combination, or two or more of each of the structural unit (b1), the structural unit (b2), and the structural unit (b3) may be contained.

The specific polymer used in the present invention preferably contains a high Tg structure (a structure having a high glass transition temperature (Tg)) in order to increase the mechanical strength. In a case of using a combination of a structure derived from a fluorine-containing monomer and a high Tg structure, it is possible to effectively improve both acoustic characteristics and mechanical strength. The high Tg structure is a polymer structure. In a case of assuming a homopolymer composed only of a constitutional unit of the polymer structure having a high Tg structure, Tg of this homopolymer is preferably 80° C. or higher, and more preferably 100° C. or higher. It is practical that an upper limit of Tg of this homopolymer is 200° C. or lower. A degree of polymerization of the homopolymer assumed above at the time of calculation of Tg is 300. Examples of the constitutional unit having a high Tg structure include a methacrylic ester component, a styrene component, a meth-acrylamide component, a structural component having an alicyclic structure, a structural component having an aromatic ring, and the like.

In the specific polymer, a proportion of the structural unit (a) having the polysiloxane bond is preferably 30% by mass or more, more preferably 40% to 90% by mass, and even more preferably 50% to 80% by mass from the viewpoint that the acoustic impedance value becomes close to that of the living body, and the acoustic attenuation is reduced.

In addition, a proportion of the structural unit (b) in the specific polymer is preferably 3% to 30% by mass, and more preferably 5% to 30% by mass from the viewpoint that high hardness is imparted, and the acoustic impedance value becomes close that of the living body.

A content of the structural unit (a) and the structural unit (b) in the specific polymer can be calculated from, for example, a prepared amount (mass ratio) of a monomer at the time of synthesis.

In the specific polymer, a mass average molecular weight of the structural unit (a) is preferably 4,000 or more, and more preferably 8,000 or more. An upper limit thereof is not particularly limited, but is preferably 50,000 or less, and more preferably 30,000 or less.

The reason for above range is because, with the mass average molecular weight of the structural unit (a) within the above-described range, the acoustic attenuation can be more effectively reduced.

The mass average molecular weight in the specific polymer can be measured by, for example, NMR analysis of the specific polymer, GPC measurement after hydrolysis of the specific polymer, and the like.

The mass average molecular weight of the specific polymer is preferably 50,000 or more, and more preferably 100,000 or more. An upper limit thereof is not particularly limited, but is preferably 5,000,000 or less, and more preferably 1,000,000 or less.

The reason for above range is because, with the mass average molecular weight of the specific polymer within the above-described range, the mechanical strength and moldability of the resin sheet can be compatible.

The acoustic impedance value of the resin material for an acoustic wave probe of the embodiment of the present invention is preferably close to that of the living body, and more preferably 1.3 Mrayls, that is, $1.3 \times 10^6$ kg/m$^2$/s or more. Accordingly, the density of the specific polymer is preferably 1.05 g/cm$^3$ or more, and more preferably 1.10 g/cm$^3$ or more. An upper limit of the density is not particularly limited, but is preferably 1.90 g/cm$^3$ or less, and more preferably 1.60 g/cm$^3$ or less.

A density value is a value obtained by rounding off the three digits after the decimal point. The density of the specific polymer can be measured by, for example, a method described in examples to be described later or can be calculated from the density of each monomer.

A content of the specific polymer in the resin material for an acoustic wave probe is preferably 50% to 100% by mass, more preferably 80% to 100% by mass, and even more preferably 90% to 100% by mass.

It is also preferable that the specific polymer used in the present invention has a structural unit (hereinafter referred to as "other structural units") other than the structural unit (a) and the structural unit (b).

Other structural units can be introduced without particular limitation as long as the effects of the present invention are exhibited, and examples thereof include a structural unit having any bond selected from an amide bond, an imide bond, a urea bond, a urethane bond, an ester bond, and an ether bond.

In the specific polymer, a proportion of the other structural units is preferably 0% to 30% by mass, and more preferably 0% to 20% by mass, from the viewpoint of reducing the acoustic attenuation.

The specific polymer used in the present invention can be synthesized by a common method, and can be obtained by, for example, reacting a monomer capable of constituting the structural unit (a) and a monomer capable of constituting the structural unit (b) with a polymerization initiator by a common method. The polymerization reaction may be any of anionic polymerization, cationic polymerization, and radical polymerization, and the radical polymerization is preferable.

In addition, the monomer capable of constituting the structural unit (a) and the monomer capable of constituting the structural unit (b), which has a function of a polymerization initiator, may be used. Examples thereof include a polydimethylsiloxane unit-containing polymeric azo polymerization initiator VPS-1001 (trade name, manufactured by Wako Pure Chemical Industries, Ltd.).

The specific polymer used in the present invention may be used alone or in combination of two or more kinds thereof.

In the resin material for an acoustic wave probe of the embodiment of the present invention, organosiloxane such as vinylsilicone and hydrosilicone, fillers, catalysts, solvents, dispersants, pigments, dyes, antistatic agents, flame retardants, heat conductivity improvers, and the like can be appropriately formulated.

—Vinyl Silicone—

Any vinyl silicone can be used without particular limitation as long as vinyl silicone is polyorganosiloxane having a vinyl group, but vinyl silicone having two or more vinyl groups in the molecular chain is preferable.

Examples of the vinyl silicone include polyorganosiloxane having vinyl groups at least at both terminals of a molecular chain (hereinafter, simply referred to as vinyl silicone (a)), or polyorganosiloxane having at least two —O—Si(CH$_3$)$_2$(CH=CH$_2$) in a molecular chain (hereinafter, simply referred to as vinyl silicone (b)). Among them, the vinyl silicone (a) having vinyl groups at least at both terminals of a molecular chain is preferable.

The vinyl silicone (a) is preferably linear and the vinyl silicone (b) is preferably vinyl silicone (b) in which —O—Si(CH$_3$)$_2$(CH=CH$_2$) is bonded to a Si atom constituting a main chain.

The vinyl silicone is hydrosilylated by, for example, reaction with a hydrosilicone having two or more Si—H groups in the presence of a platinum catalyst. A cross-linked (vulcanized) structure is formed through this hydrosilylation reaction (addition reaction).

A content of the vinyl group of the vinyl silicone is not particularly limited. The content of the vinyl group is, for example, preferably 0.01 to 5 mol % and more preferably 0.05 to 2 mol % from the viewpoint of forming a sufficient network between the vinyl group and the hydrosilicone.

The content of the vinyl group is represented by mol % of the vinyl group-containing siloxane unit based on 100 mol % of all the units constituting the vinyl silicone. One vinyl group-containing siloxane unit has 1 to 3 vinyl groups. Among them, one vinyl group is preferable for one vinyl group-containing siloxane unit. For example, in a case where all Si atoms of Si in a Si—O unit and at a terminal which constitute a main chain have at least one vinyl group, the content becomes 100 mol %.

In addition, the vinyl silicone preferably has a phenyl group, and a content of the phenyl group of the vinyl silicone is not particularly limited. The content of the phenyl group is, for example, preferably 1 to 80 mol % and preferably 2 to 40 mol % from the viewpoint of mechanical strength in a case where a resin sheet for an acoustic wave probe is made.

The content of the phenyl group is represented by mol % of the phenyl group-containing siloxane unit based on 100 mol % of all the units constituting the vinyl silicone. One phenyl group-containing siloxane unit has 1 to 3 phenyl groups. Among them, two phenyl groups are preferable for one phenyl group-containing siloxane unit. For example, in a case where all Si atoms of Si in a Si—O unit and at a terminal which constitute a main chain have at least one phenyl group, the content becomes 100 mol %.

The "unit" refers to Si atoms in a Si—O unit and at a terminal which constitute a main chain.

A degree of polymerization and a specific gravity are not particularly limited. The degree of polymerization is preferably 200 to 3,000 and more preferably 400 to 2,000, and the specific gravity is preferably 0.9 to 1.1 from the viewpoint of improving mechanical strength, hardness, chemical stability, and the like of the obtained resin sheet for an acoustic wave probe.

A mass average molecular weight of the vinyl silicone having a vinyl group is preferably 20,000 to 200,000, more preferably 40,000 to 150,000, and still more preferably 45,000 to 120,000 from the viewpoints of the mechanical strength, the hardness, and/or easiness of processing.

A kinematic viscosity at 25° C. is preferably $1\times10^{-5}$ to 10 $m^2/s$, more preferably $1\times10^{-4}$ to 1 $m^2/s$, and even more preferably $1\times10^{-3}$ to 0.5 $m^2/s$.

The kinematic viscosity can be measured and obtained at a temperature of 25° C. using a Ubbelohde-type viscometer (for example, a trade name of SU manufactured by SIBATA SCIENTIFIC TECHNOLOGY LTD.) in compliance with JIS Z8803.

Polyorganosiloxane represented by General Formula (A) is preferable as the vinyl silicone (a) having vinyl groups at least at both terminals of a molecular chain.

$$R^{a1}-\underset{\underset{R^{a2}}{|}}{\overset{\overset{R^{a2}}{|}}{Si}}-O\underset{x1}{\left(\underset{\underset{R^{a2}}{|}}{\overset{\overset{R^{a2}}{|}}{Si}}-O\right)}\underset{x2}{\left(\underset{\underset{R^{a2}}{|}}{\overset{\overset{R^{a3}}{|}}{Si}}-O\right)}\underset{\underset{R^{a2}}{|}}{\overset{\overset{R^{a2}}{|}}{Si}}-R^{a1} \quad (A)$$

In General Formula (A), $R^{a1}$ represents a vinyl group and $R^{a2}$ and $R^{a3}$ each independently represent an alkyl group, a cycloalkyl group, an alkenyl group, or an aryl group. x1 and x2 each independently represent an integer of 1 or more. Here, a plurality of $R^{a2}$'s and a plurality of $R^{a3}$'s may be the same as or different from each other. In addition, each of the groups of $R^{a2}$ and $R^{a3}$ may further have a substituent.

The number of carbon atoms in an alkyl group in $R^{a2}$ and $R^{a3}$ is preferably 1 to 10, more preferably 1 to 4, even more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, preferably 5 to 10, and even more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and even more preferably 2. Examples of the alkenyl group include a vinyl group, an allyl group, and a butenyl group.

The number of carbon atoms in an aryl group in $R^{a2}$ and $R^{a3}$ is preferably 6 to 12, more preferably 6 to 10, and still more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or an aryl group, more preferably an alkyl group having 1 to 4 carbon atoms, a vinyl group, or a phenyl group, and still more preferably a methyl group, a vinyl group, or a phenyl group.

Among them, $R^{a2}$ is preferably a methyl group. $R^{a3}$ is preferably a methyl group, a vinyl group, or a phenyl group, more preferably a methyl group or a phenyl group, and particularly preferably a phenyl group. In addition, it is also preferable that both $R^{a2}$'s in the repetition of x1 are phenyl groups.

x1 is preferably an integer of 200 to 3,000 and more preferably an integer of 400 to 2,000.

x2 is preferably an integer of 1 to 3,000, more preferably an integer of 1 to 1,000, still more preferably an integer of 40 to 1,000, and particularly preferably an integer of 40 to 700.

In addition, as another embodiment, x1 is preferably an integer of 1 to 3,000 and more preferably an integer of 5 to 1,000.

Examples of the vinyl silicone (a) having vinyl groups at least at both terminals of a molecular chain include DMS series (for example, DMS-V31, DMS-V31S15, DMS-V33, DMS-V35, DMS-V35R, DMS-V41, DMS-V42, DMS-V46, DMS-V51, and DMS-V52), and PDV series (for example, PDV-0341, PDV-0346, PDV-0535, PDV-0541, PDV-1631, PDV-1635, PDV-1641, and PDV-2335), PMV-9925, PVV-3522, FMV-4031, and EDV-2022 all of which are trade names manufactured by GELEST, INC.

In the DMS-V31S15, fumed silica is formulated into DMS-V31S15 in advance, and therefore, kneading using a special device is unnecessary.

The vinyl silicone may be used singly or in a combination of two or more thereof.

—Hydrosilicone—

Hydrosilicone can be used without any particular limitation as long as hydrosilicone is a polyorganosiloxane having two or more Si—H groups in a molecular chain.

In a case where there are two or more Si—H groups in a molecular chain, it is possible to crosslink polyorganosiloxane having at least two polymerizable unsaturated groups.

In the hydrosilicone, a linear structure and a branched structure are present, and the linear structure is preferable.

The mass average molecular weight of a linear structure is preferably 500 to 100,000 and more preferably 1,500 to 50,000 from the viewpoints of the mechanical strength and the hardness.

The hydrosilicone which has a linear structure and two or more Si—H groups in a molecular chain is preferably polyorganosiloxane represented by General Formula (B).

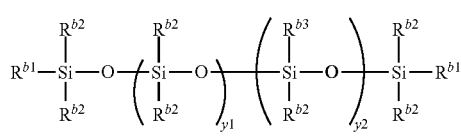

In General Formula (B), $R^{b1}$ to $R^{b3}$ each independently represent a hydrogen atom, an alkyl group, a cycloalkyl group, an alkenyl group, an aryl group, or —O—Si$(R^{b5})_2$$(R^{b4})$. $R^{b4}$ and $R^{b5}$ each independently represent a hydrogen atom, an alkyl group, a cycloalkyl group, an alkenyl group, or an aryl group. y1 and y2 each independently represent an integer of 1 or more. Here, a plurality of $R^{b1}$'s, a plurality of $R^{b2}$'s a plurality of $R^{b3}$'s, a plurality of $R^{b4}$'s, and a plurality of $R^{b5}$'s each may be the same as or different from each other. In addition, each of the groups of $R^{b1}$ to $R^{b5}$ may further be substituted by a substituent. However, two or more Si—H groups are present in a molecular chain.

An alkyl group, a cycloalkyl group, an alkenyl group, and an aryl group in $R^{b1}$ to $R^{b3}$ are synonymous with an alkyl group, a cycloalkyl group, an alkenyl group, and an aryl group in $R^{a2}$ and $R^{a3}$, and preferred ranges thereof are also the same as each other.

An alkyl group, a cycloalkyl group, an alkenyl group, and an aryl group in $R^{b4}$ and $R^{b5}$ of —O—Si$(R^{b5})_2$$(R^{b4})$ are synonymous with an alkyl group, a cycloalkyl group, an alkenyl group, and an aryl group in $R^{b1}$ to $R^{b3}$, and preferred ranges thereof are also the same as each other.

$R^{b1}$ to $R^{b3}$ are preferably a hydrogen atom, an alkyl group, an alkenyl group, an aryl group, or —O—Si$(R^{b5})_2$$(R^{b4})$, and more preferably a hydrogen atom, an alkyl group having 1 to 4 carbon atoms, a vinyl group, a phenyl group, or —O—Si$(CH_3)_2$H.

Among them, $R^{b1}$ and $R^{b2}$ are preferably a hydrogen atom, an alkyl group, an alkenyl group, or an aryl group, more preferably a hydrogen atom or an alkyl group, and still more preferably a hydrogen atom or a methyl group.

$R^{b3}$ is preferably a hydrogen atom, an alkyl group, an alkenyl group, an aryl group, or —O—Si$(R^{b5})_2$$(R^{b4})$, more preferably a hydrogen atom or an aryl group, and still more preferably a hydrogen atom or a phenyl group.

In the present invention, in a case where $R^{b3}$ is a phenyl group, it is preferable that $R^{b1}$ is a hydrogen atom. It is more preferable that $R^{b1}$ is a hydrogen atom and the following conditions are satisfied.

1) One $R^{b2}$ in the repetition of y1 is a hydrogen atom and the remaining $R^{b2}$ is an alkyl group, $R^{b2}$ in the repetition of y2 is an alkyl group, and $R^{b3}$ is a phenyl group.

2) y1 is 0, $R^{b2}$ in the repetition of y2 is an alkyl group, and $R^{b3}$ is a phenyl group.

3) y1 is 0, $R^{b2}$ in the repetition of y2 is —O—Si$(R^{b5})_2$$(R^{b4})$, and $R^{b3}$ is a phenyl group.

In the above-described 3), a case where $R^{b4}$ is a hydrogen atom and $R^{b5}$ is an alkyl group is particularly preferable.

y1 is preferably an integer of 0 to 2,000, more preferably an integer of 0 to 1,000, and still more preferably an integer of 0 to 30.

y2 is preferably an integer of 1 to 2,000, more preferably an integer of 1 to 1,000, and still more preferably an integer of 1 to 30.

y1+y2 is preferably an integer of 5 to 2,000, more preferably an integer of 7 to 1,000, even more preferably 10 to 50, and particularly preferably an integer of 15 to 30.

As a combination of $R^{b1}$ to $R^{b3}$, a combination of a hydrogen atom or an alkyl group having 1 to 4 carbon atoms as $R^{b1}$, an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

In the preferred combinations, the content of a hydrosilyl group represented by y2/(y1+y2) is preferably greater than 0.1 and less than or equal to 1.0 and more preferably greater than 0.2 and less than or equal to 1.0.

Examples of the hydrosilicone with a linear structure include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %) as methylhydrosiloxane-dimethylsiloxane copolymers (trimethylsiloxane terminated), HPM-502 (MeHSiO: 45 to 50 mol %) as a methylhydrosiloxane-phenylmethylsiloxane copolymer, and HMS-991 (MeHSiO: 100 mol %) as a methylhydrosiloxane polymer, all of which are trade names of GELEST, INC.

The mol % of MeHSiO has the same meaning as that y2/(y1+y2) in the above-described preferred combination of $R^{b1}$ to $R^{b3}$ is multiplied by 100.

It is preferable that both the linear structure and the branched structure have no vinyl group from the viewpoint of preventing the progress of a cross-linking reaction within a molecule. Among these, it is preferable that the branched structure has no vinyl group.

The hydrosilicone, which has a branched structure and two or more Si—H groups in a molecular chain, has a branched structure and two or more hydrosilyl groups (Si—H groups).

A specific gravity is preferably 0.9 to 0.95.

The hydrosilicone with a branched structure is preferably represented by Average Composition Formula (b).

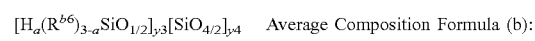

$[H_a(R^{b6})_{3-a}SiO_{1/2}]_{y3}[SiO_{4/2}]_{y4}$    Average Composition Formula (b):

Here, $R^{b6}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b6}$ are synonymous with an alkyl group, a cycloalkyl group, an alkenyl group, and an aryl group in $R^{a2}$ and $R^{a3}$, and preferred ranges thereof are also the same as each other.

a is preferably 1.

The content of a hydrosilyl group represented by a/3 is preferably greater than 0.1 and less than 0.6 and more preferably greater than 0.1 and less than 0.4.

In contrast, in a case of representing the hydrosilicone with a branched structure using a chemical structural formula, polyorganosiloxane in which —O—Si$(CH_3)_2$(H) is bonded to a Si atom constituting a main chain is preferable and polyorganosiloxane having a structure represented by General Formula (Bb) is more preferable.

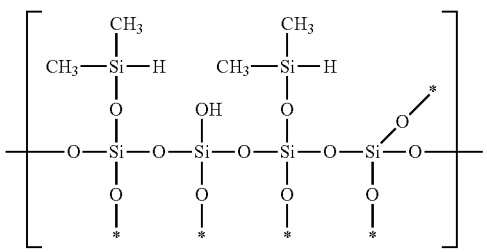

(Bb)

In General Formula (Bb), * means a bond with at least a Si atom of siloxane.

Examples of the hydrosilicone with a branched structure include HQM-107 (trade name of Hydride Q Resin manufactured by GELEST, INC.) and HDP-111 (trade name of polyphenyl-(dimethylhydroxy)siloxane (hydride terminated), [(HMe$_2$SiO)(C$_6$H$_5$Si)O]: 99 to 100 mol % manufactured by GELEST, INC.)

The hydrosilicone may be used singly or in a combination of two or more thereof. In addition, the hydrosilicone with a linear structure and the hydrosilicone with a branched structure may be used in combination.

The vinyl group of the vinyl silicone and the Si—H group of the hydrosilicone usually react stoichiometrically at a ratio of 1:1.

However, from the viewpoint that all the vinyl groups react with the Si—H group, the equivalent weight of the Si—H group of the hydrosilicone to the vinyl group of the vinyl silicone is preferably vinyl group:Si—H group=1:1.1 to 1:8, and more preferably 1:1.2 to 1:5.

—Filler—

The resin material for an acoustic wave probe of the embodiment of the present invention may contain a filler, although the resin sheet having excellent properties can be produced with the resin material even without containing an inorganic filler.

Any filler can be used without particular limitation as long as it is a filler used for the resin material for an acoustic wave probe, and specific examples thereof include inorganic compound particles.

Examples of the inorganic compound in the inorganic compound particles include silicon oxide (silica), silicon carbide, boron nitride, alumina, barium sulfate, cerium oxide, calcium carbonate, aluminum nitride, calcium oxide, vanadium oxide, silicon nitride, barium carbonate, titanium carbide, titanium nitride, copper oxide, zirconium carbide, tungsten carbide, magnesium oxide, titanium oxide, iron oxide, zinc oxide, zirconium oxide, barium oxide, tin oxide, and ytterbium oxide. Any one selected from the group consisting of silica, silicon carbide, boron nitride, alumina, barium sulfate, and cerium oxide is preferable; any one selected from the group consisting of silica, alumina, barium sulfate, and cerium oxide is more preferable; and silica is even more preferable.

By containing the inorganic compound particles in the resin material for an acoustic wave probe, an effect of improving the acoustic impedance, the hardness, and the mechanical strength (for example, the tear strength) of the resin sheet for an acoustic wave probe can be obtained.

An average primary particle diameter of the inorganic compound particles is preferably more than 16 nm and less than 100 nm, more preferably 5 nm to 90 nm, even more preferably 10 nm to 80 nm, and particularly preferably 15 nm to 70 nm from the viewpoint of suppressing an increase in the acoustic attenuation of the resin sheet for an acoustic wave probe and improving the tear strength.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA, Ltd.). In the present specification, for silica particles of which the average primary particle diameter has not been disclosed in the catalog or for silica particles newly manufactured, the average primary particle diameter is obtained through the above-described measurement method.

Here, the average primary particle diameter of the inorganic compound particles means an average primary particle diameter in a state in which the surface treatment has been performed.

The inorganic compound particles may be used singly or in a combination of two or more thereof.

The specific surface area of the inorganic compound particles is preferably 1 to 400 m$^2$/g, more preferably 5 to 200 m$^2$/g, and particularly preferably 10 to 100 m$^2$/g from the viewpoint of improving the hardness and/or the mechanical strength of the resin sheet for an acoustic wave probe to be obtained.

The surface of the inorganic compound particles is preferably treated (modified), and more preferably surface-treated with a silane compound.

By surface-treating the inorganic compound particles with a silane compound, the interaction with the polymer used in the present invention which has a siloxane bond is strengthened, or the affinity increases, and therefore the inorganic compound particles having a small average primary particle diameter is considered to be capable of fine dispersion. For this reason, it is considered that the inorganic compound fine particles more exert a function as a stopper in a case where mechanical adaptability is applied, and therefore the hardness and mechanical strength of the resin sheet for an acoustic wave probe are improved.

A usual technique may be used as a technique of the surface treatment. Examples of the technique of the surface treatment using a silane compound include a technique of performing surface treatment using a silane coupling agent and a technique of performing coating using a silicone compound.

(i) Silane Coupling Agent

A silane coupling agent having a hydrolyzable group is preferable as a silane coupling agent from the viewpoint of improving the hardness and/or the mechanical strength of the resin sheet for an acoustic wave probe. Surface modification of the inorganic compound particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the inorganic compound particles, thereby improving the hardness and/or the mechanical strength of the resin sheet for an acoustic wave probe. Examples of the hydrolyzable group include an alkoxy group, an acyloxy group, and a halogen atom.

A case where the surface of the inorganic compound particles is surface-modified to be hydrophobic is preferable, because the affinity between the inorganic compound particles, and the vinyl silicone and the hydrosilicone becomes favorable, and therefore the hardness and the mechanical strength of the resin sheet for an acoustic wave probe to be obtained are improved.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyl triethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

As the silane coupling agent, a trialkylsilylating agent is preferable, and a trimethylsilylating agent is more preferable.

Examples of the silane compound include the above-described silane coupling agents and a silane coupling agent in which a functional group in a silane coupling agent is substituted by an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted by an alkyl group.

Examples of a commercially available silane coupling agent include hexamethyldisilazane (HMDS) (trade name: HEXAMETHYLDISILAZANE (SIH6110.1) manufactured by GELEST, INC.).

A hydroxyl group existing on the surfaces of the inorganic compound particles is covered with a trimethylsilyl group through a reaction with hexamethyldisilazane (HMDS), methyltrimethoxysilane (MTMS), trimethylmethoxysilane, and the like and the surfaces of the inorganic compound particles are hydrophobically modified.

In the present invention, the silane coupling agent may be used alone or in a combination of two or more thereof.

(ii) Silicone Compound

A silicone compound with which the inorganic compound particles are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which an amino group, an epoxy group, a methoxy group, a (meth)acryloyl group, a phenol group, a carboxylic anhydride group, a hydroxy group, a mercapto group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy.

The inorganic compound particles coated with a silicone compound can be obtained through a usual method. For example, the inorganic compound particles can be obtained by being mixed and stirred in dimethylpolysiloxane for a certain period of time and being filtered.

In addition, in a case of using reactive modified silicone as a silicone compound, surface modification of the inorganic compound particles is performed through reaction of an organic group with a hydroxyl group of the surfaces of the inorganic compound particles, and therefore, the hardness and/or the mechanical strength of the resin sheet for an acoustic wave probe to be obtained is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The degree of surface modification of the inorganic compound particles, that is, the degree of hydrophobicity of the inorganic compound particles can be examined by the following degree of methanol hydrophobicity.

The degree of methanol hydrophobicity of the inorganic compound particles which is calculated through the following methanol titration test is preferably 40% to 80% by mass, more preferably 50% to 80% by mass, and even more preferably 60% to 80% by mass. Here, the larger the degree of methanol hydrophobicity, the higher the hydrophobicity, and the smaller the degree of methanol hydrophobicity, the higher the hydrophilicity.

50 ml of ion exchange water and 0.2 g of the inorganic compound particles as samples are placed in a beaker at 25° C. and stirred with a magnetic stirrer, methanol is added dropwise thereto from a burette, and the amount (Xg) of methanol added dropwise until the whole sample settles is measured. The degree of methanol hydrophobicity is calculated using the following equation.

$$\text{Degree of methanol hydrophobicity(mass \%)} = X/(50+X) \times 100$$

With the degree of hydrophobicity of methanol within the above-described preferable range, an increase in viscosity of the resin material for an acoustic wave probe can be suppressed, or a reduction in acoustic sensitivity of the resin sheet for an acoustic wave probe can be suppressed.

The Wardell's sphericity of a primary particle of the inorganic compound particles is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the inorganic compound particles becomes smaller in a case where the resin sheet for an acoustic wave probe is irradiated with the acoustic wave. In particular, in the range of the specific average primary particle diameter of the inorganic compound particles, a shape of the inorganic compound particles is preferably spherical and more preferably true spherical from the viewpoint of more effectively improving the acoustic sensitivity.

In this specification, the "true spherical shape" also includes a slightly distorted sphere of which the Wardell's sphericity is within a range of 0.9 to 1.

Among the inorganic compound particles, the silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3{}_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-099582A and JP2014-114175 A.

—Catalyst—

Examples of the catalyst include platinum or a platinum-containing compound (hereinafter, also simply referred to as a platinum compound). Any platinum or platinum compound can be used.

Specific examples thereof include a catalyst in which platinum black or platinum is carried on an inorganic compound, carbon black, or the like; platinum chloride or an alcohol solution of platinum chloride; a complex salt of platinum chloride and olefin; and a complex salt of platinum chloride and vinyl siloxane. The catalyst may be used singly, or in a combination of two or more thereof.

The catalyst is required in the hydrosilylation reaction in which the Si—H group of the hydrosilicone is added to the vinyl group of the vinyl silicone. As the hydrosilylation reaction (addition vulcanization reaction) proceeds, the vinyl silicone is crosslinked with the hydrosilicone to form the silicone resin.

The catalyst may be contained in the resin material for an acoustic wave probe of the embodiment of the present invention, or, without being contained in the resin material for an acoustic wave probe, the catalyst may be allowed to come into contact with the resin material for an acoustic wave probe in a case of molding by using the resin material for an acoustic wave probe. The latter case is preferable.

Examples of commercially available platinum catalyst include platinum compounds (a trade name of PLATINUM CYCLOVINYLMETHYLSILOXANE COMPLEX IN CYCLIC METHYLVINYLSILOXANES (SIP6832.2) with 2 mass % of Pt concentration; and a trade name of PLATINUM DIVINYLTETRAMETHYLDISILOXANE COMPLEX IN VINYL-TERMINATED POLYDIMETHYLSILOXANE (SIP6830.3) with 3 mass % of Pt concentration, all of which are manufactured by GELEST, INC.).

In a case where a catalyst is contained in the resin material for an acoustic wave probe of the embodiment of the present invention, the content of the catalyst present with respect to 100 parts by mass of a polysiloxane mixture is not particularly limited, but is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass from the viewpoint of reactivity.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

—Vulcanization Retardant—

In the present invention, a vulcanization retardant for vulcanization reaction can be appropriately used. The vulcanization retardant is used for delaying the above-described addition vulcanization reaction and examples thereof include a low molecular weight vinylmethylsiloxane homopolymer (trade name: VMS-005 manufactured by GELEST, INC.).

The vulcanization rate, that is, the working time can be adjusted depending on the content of the vulcanization retardant.

<Resin Material for Acoustic Wave Probe and Method for Manufacturing Resin Sheet for Acoustic Wave Probe>

The resin material for an acoustic wave probe of the embodiment of the present invention can be prepared by a usual method in a case of containing the above-mentioned components in addition to the specific polymer.

For example, the resin material can be obtained by kneading the specific polymer and the above-mentioned other components using a kneader, a pressure kneader, a Banbury mixer (continuous kneader), and a kneading device with two rolls. The order of mixing the components is not particularly limited.

The resin material for an acoustic wave probe of the embodiment of the present invention which is obtained as above is subjected to, for example, hot pressing, thereby obtaining the resin sheet for an acoustic wave probe. A method of hot pressing is not particularly limited, and hot pressing can be performed by a usual method. Examples thereof include an aspect in which hot pressing is performed at 50° C. to 200° C. for 1 to 10 minutes at a pressure of 5 to 30 MPa by using an apparatus such as MINI TEST PRESS-10 (trade name, manufactured by Toyo Seiki Co., Ltd.).

<Acoustic Characteristics and Hardness of Resin Sheet for Acoustic Wave Probe>

The resin sheet for an acoustic wave probe is a sheet obtained by molding the resin material for an acoustic wave probe of the embodiment of the present invention by hot pressing or the like.

The acoustic characteristics and hardness of the resin sheet for an acoustic wave probe will be described in detail below.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, and the like.

[Acoustic (Ultrasonic) Attenuation and Sensitivity]

The acoustic (ultrasonic) attenuation and sensitivity can be obtained by a method to be described later in a section of examples.

In an evaluation system in the present invention, the acoustic (ultrasonic) sensitivity is preferably greater than or equal to −70 dB.

[Acoustic Impedance]

The acoustic impedance is preferably close to the acoustic impedance of the living body, more preferably $1.1 \times 10^6$ $kg/m^2/sec$ to $2.0 \times 10^6$ $kg/m^2/sec$, and even more preferably $1.3 \times 10^6$ $kg/m^2/sec$ to $1.7 \times 10^6$ $kg/m^2/sec$.

The acoustic impedance can be obtained by a method in the section of examples.

[Hardness]

The hardness is preferably 10 degrees or more and more preferably 40 degrees or more in a testing method according to JIS K 6253-3. A practical upper limit value is 100 degrees or less. With the hardness within the above-described range, it is possible to prevent deformation in a case where the silicone resin is incorporated as a part of the acoustic wave probe and used.

The hardness of the resin sheet can be obtained by a measurement method to be described later in a section of examples.

The resin material for an acoustic wave probe of the embodiment of the present invention is useful for medical members and can preferably be used, for example, in an acoustic wave probe or an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which has been reflected or generated from an object and displays the received acoustic wave as an image or a signal strength.

Particularly, the resin material for an acoustic wave probe of the embodiment of the present invention can suitably be used in a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope; and a material or the like of an acoustic lens in an ultrasound probe comprising capacitive micromachined ultrasonic transducers (cMUT) as an ultrasonic transducer array.

Specifically, the resin material for an acoustic wave probe of the embodiment of the present invention is preferably applied to, for example, an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013-158435A, JP2013-154139A, or the like.

<<Acoustic Wave Probe (Probe)>>

A configuration of an acoustic wave probe of the present invention will be described below in more detail based on a configuration of an ultrasound probe in an ultrasound diagnostic apparatus which is described in the FIGURE. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in the FIGURE. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

The resin material for an acoustic wave probe of the embodiment of the present invention can preferably be used as a material for the acoustic matching layer since the difference in acoustic impedance ($1.4 \times 10^6$ to $1.7 \times 10^6$ kg/m²/sec) between the piezoelectric element layer and a living body is small. The acoustic matching layer preferably contains 10% by mass or more of the resin material for an acoustic wave probe of the embodiment of the present invention.

<Acoustic Lens>

An acoustic lens of the embodiment of the present invention preferably has a damping coefficient of 0.50 dB/(MHz·mm) or less at a frequency of 15 MHz, an acoustic impedance of $1.30 \times 10^6$ kg/m²/s or more and $1.70 \times 10^6$ kg/m²/s or less, and an acoustic velocity of 1300 m/s or less.

The damping coefficient is preferably 0.45 dB/(MHz·mm) or less and more preferably 0.40 dB/(MHz·mm) or less. A lower limit thereof is not particularly limited, but is practically 0.20 dB/(MHz·mm) or more.

The damping coefficient can be obtained by a method to be described later in the section of examples.

The acoustic velocity is preferably 1200 m/s or less and more preferably 1150 m/s or less. A lower limit thereof is not particularly limited, but is practically 950 m/s or more.

The acoustic velocity can be obtained by a method to be described later in the section of examples.

The acoustic lens is preferably a lens made of the resin material for an acoustic wave probe of the embodiment of the present invention as a constituent material.

The method for manufacturing the acoustic lens of the embodiment of the present invention is not particularly limited, and can be obtained using, for example, the resin material for an acoustic wave probe of the embodiment of the present invention as a constituent material.

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4 \times 10^6$ to $1.7 \times 10^6$ kg/m²/sec in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The resin material for an acoustic wave probe of the embodiment of the present invention can also preferably be used as a material of the acoustic lens.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the resin material for an acoustic wave probe of the embodiment of the present invention as a general medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the resin material for an acoustic wave probe of the embodiment of the present invention exhibits a function particularly regarding conventional problems will be described in detail.

The resin material for an acoustic wave probe of the embodiment of the present invention exhibits an excellent effect even with respect to other apparatuses disclosed below.

—Ultrasound Probe Comprising Capacitive Micromachined Ultrasonic Transducer (cMUT)—

In a case where cMUT apparatuses disclosed in JP2006-157320A, JP2011-071842A, and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the resin material for an acoustic wave probe of the embodiment of the present invention. Accordingly, it is possible to make the sensitivity of cMUT to performance of a conventional transducer.

The cMUT apparatus is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus Using Photo-Ultrasound Imaging—

Photo-ultrasound imaging (photoacoustic imaging: PAD disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the resin material for an acoustic wave probe of the embodiment of the present invention.

—Ultrasound Endoscope—

In an ultrasonic wave in an ultrasound endoscope disclosed in JP2008-311700A or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity using piezoelectric single crystal material.

However, it is possible to improve the sensitivity of the ultrasonic transducer for an endoscope using the acoustic lens obtained from the resin material for an acoustic wave probe of the embodiment of the present invention.

In addition, even in a case of using the same ultrasonic transmission frequency (for example, 10 MHz), the efficacy is particularly exhibited in a case of using the acoustic lens obtained from the resin material for an acoustic wave probe of the embodiment of the present invention in the ultrasonic transducer for an endoscope.

Examples

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

Example (Synthesis of Polymer 1)

0.5 parts by mass of dimethyl 1,1'-azobis(1-cyclohexanecarboxylate) (manufactured by Wako Pure Chemical Industries, Ltd.) was added, at 90° C. under a nitrogen atmosphere, to 70 parts by mass of one-terminal methacrylic-modified silicone (trade name: X-22-174BX, manufactured by Shin-Etsu Chemical Co., Ltd., mass average molecular weight of 2,300), 30 parts by mass of methyl methacrylate, and 100 parts by mass of propylene glycol 1-monomethyl ether 2-acetate, and the mixture was allowed to react for 2 hours at 90° C. Thereafter, 0.5 parts by mass of dimethyl 1,1'-azobis(1-cyclohexanecarboxylate) (manufactured by Wako Pure Chemical Industries, Ltd.) was added thereto and reacted at 90° C. for 2 hours. Furthermore, 0.5 parts by mass of dimethyl 1,1'-azobis(1-cyclohexanecarboxylate) (manufactured by Wako Pure Chemical Industries, Ltd.) was added thereto and reacted at 90° C. for 2 hours. The reaction solution was added to 1000 mL of isopropyl alcohol and 200 mL of methanol, and therefore a white solid was generated. The generated white solid was washed with methanol and dried to obtain a polymer 1.

Dimethyl 1,1'-azobis(1-cyclohexanecarboxylate) is a polymerization initiator and is described as "initiator" in Table 1.

In the following chemical reaction formula, structures in parentheses "( )" indicate a repeated structure.

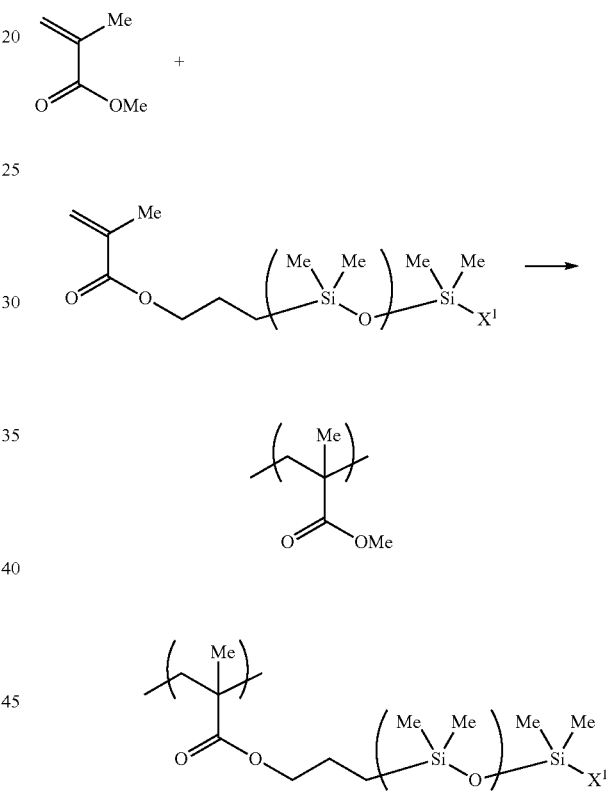

In the formula, Me represents a methyl group, and $X^1$ represents a monovalent organic group.

(Synthesis of Polymers 2 to 7)

Polymers 2 to 7 were synthesized in the same manner as in the synthesis of the polymer 1 except that the composition was changed to those shown in Table 1.

(Synthesis of Polymer 8)

A polymer 8 was synthesized in the same manner as in the synthesis of a polymer 9 to be described later except that the composition was changed to that shown in Table 1.

(Synthesis of Polymer 9)

70 parts by mass of a polydimethylsiloxane unit-containing polymeric azo polymerization initiator VPS-1001 (manufactured by Wako Pure Chemical Industries, Ltd., polysiloxane unit, mass average molecular weight of 10,000), 30 parts by mass of styrene, and 100 parts by mass of propylene glycol 1-monomethyl ether 2-acetate were mixed, and the mixture was allowed to react for 4 hours at 75° C. under a nitrogen atmosphere. The reaction solution was added to 1000 mL of methanol, and therefore a white solid was generated. The generated white solid was washed with methanol and dried to obtain a polymer 9.

In the following chemical reaction formula, structures in parentheses "( )" indicate a repeated structure. On the other hand, a structure in parentheses "[ ]" indicates a structural unit.

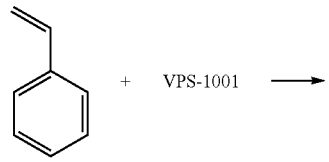  + VPS-1001  ⟶

-continued

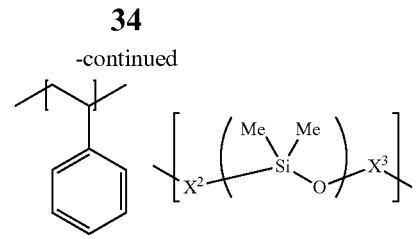

In the formula, Me represents a methyl group, and $X^2$ and $X^3$ each represent a divalent organic group.

(Synthesis of Polymers 10 to 28)

Polymers 10 to 28 were synthesized in the same manner as in the synthesis of the polymer 1 except that the composition was changed to those shown in Table 1.

TABLE 1

| Polymer No. | Monomer for forming structural unit (a) Type | Formulation ratio | Monomer for forming structural unit (b) Type | Formulation ratio | Amount of initiator (%) | Polymer structure | Mass average molecular weight ($10^4$) of structural unit (a) | Mass average molecular weight ($10^4$) of polymer |
|---|---|---|---|---|---|---|---|---|
| 1 | X-22-174BX | 70 | Methyl methacrylate | 30 | 5 | Graft | 0.2 | 5.5 |
| 2 | X-22-174BX | 70 | Styrene | 30 | 5 | Graft | 0.2 | 4.8 |
| 3 | X-22-174BX | 70 | Methacrylic diphenylamide | 30 | 5 | Graft | 0.2 | 4.6 |
| 4 | KF-2012 | 70 | Styrene | 30 | 5 | Graft | 0.4 | 5.2 |
| 5 | X-22-2426 | 70 | Styrene | 30 | 5 | Graft | 1.2 | 5.4 |
| 6 | X-22-2426 | 70 | Styrene | 30 | 1 | Graft | 1.2 | 11.2 |
| 7 | X-22-2426 | 70 | Styrene | 30 | 0.5 | Graft | 1.2 | 30.5 |
| 8 | VPS-1001 | 70 | Methyl methacrylate | 30 | 70 | Graft | 1.0 | 11.0 |
| 9 | VPS-1001 | 70 | Styrene | 30 | 70 | Graft | 1.0 | 9.8 |
| 10 | X-22-2426 | 70 | p-Bromostyrene | 30 | 0.5 | Graft | 1.2 | 31.5 |
| 11 | X-22-2426 | 70 | p-Fluorostyrene | 30 | 0.5 | Graft | 1.2 | 29.5 |
| 17 | X-22-2426 | 70 | Pentafluorostyrene | 30 | 0.5 | Graft | 1.2 | 28.0 |
| 18 | X-22-2426 | 70 | 3,5-Bis(trifluoromethyl)styrene | 30 | 0.5 | Graft | 1.2 | 27.5 |
| 14 | X-22-2426 | 70 | Pentafluorophenyl methacrylate | 30 | 0.5 | Graft | 1.2 | 31.0 |
| 15 | X-22-7476 | 70 | 2,2,2-Trifluoroethyl acrylate | 30 | 0.5 | Graft | 1.2 | 30.5 |
| 16 | X-22-2426 | 70 | 2,2,3,3,3-Pentafluoropropyl methacrylate | 30 | 0.5 | Graft | 1.2 | 31.5 |
| 17 | X-22-2426 | 70 | 1H,1H,2H,2H-Nonafluorohexyl methacrylate | 30 | 0.5 | Graft | 1.2 | 30.2 |
| 18 | X-22-2426 | 70 | 1,1,1,3,3,3-Hexafluoroisopropyl methacrylate | 30 | 0.5 | Graft | 1.2 | 30.8 |
| 19 | X-22-2426 | 70 | Methyl α-trifluoromethyl methacrylate | 30 | 0.5 | Graft | 1.2 | 32.0 |
| 20 | X-22-2426 | 50 | Pentafluorostyrene | 30 | 0.5 | Graft | 1.2 | 25.0 |
|  |  |  | Methyl methacrylate | 20 |  |  |  |  |
| 21 | X-22-2426 | 50 | Pentafluorostyrene | 30 | 0.5 | Graft | 1.2 | 29.0 |
|  |  |  | Styrene | 20 |  |  |  |  |
| 22 | X-22-2426 | 50 | Pentafluorostyrene | 30 | 0.5 | Graft | 1.2 | 32.0 |
|  |  |  | Methyl methacrylate | 10 |  |  |  |  |
|  |  |  | Methacrylic acid diphenylamide | 10 |  |  |  |  |

TABLE 2

Continued from Table 1

| Polymer No. | Monomer for forming structural unit (a) Type | Formulation ratio | Monomer for forming structural unit (b) Type | Formulation ratio | Amount of initiator (%) | Polymer structure | Mass average molecular weight ($10^4$) of structural unit (a) | Mass average molecular weight ($10^4$) of polymer |
|---|---|---|---|---|---|---|---|---|
| 23 | X-22-2426 | 50 | 2,2,2-Trifluoropropyl methacrylate | 30 | 0.15 | Graft | 1.2 | 33.0 |
|  |  |  | Methyl methacrylate | 20 |  |  |  |  |
| 24 | X-22-2426 | 50 | 2,2,2-Trifluoropropyl methacrylate | 30 | 0.15 | Graft | 1.2 | 30.0 |
|  |  |  | Styrene | 20 |  |  |  |  |

TABLE 2-continued

Continued from Table 1

| Polymer No. | Monomer for forming structural unit (a) Type | Formulation ratio | Monomer for forming structural unit (b) Type | Formulation ratio | Amount of initiator (%) | Polymer structure | Mass average molecular weight $(10^4)$ of structural unit (a) | Mass average molecular weight $(10^4)$ of polymer |
|---|---|---|---|---|---|---|---|---|
| 25 | X-22-2426 | 50 | 2,2,2-Trifluoropropyl methacrylate<br>Methyl methacrylate<br>Methacrylic diphenylamide | 30<br>10<br>10 | 0.15 | Graft | 1.2 | 32.0 |
| 26 | X-22-2426 | 50 | 2,2,3,3,3-Pentafluoropropyl methacrylate<br>Methyl methacrylate | 30<br>20 | 0.15 | Graft | 1.2 | 25.0 |
| 27 | X-22-2426 | 50 | 2,2,3,3,3-Pentafluoropropyl methacrylate<br>Styrene | 30<br>20 | 0.15 | Graft | 1.2 | 29.0 |
| 28 | X-22-2426 | 50 | 2,2,3,3,3-Pentafluoropropyl methacrylate<br>Methyl methacrylate<br>Methacrylic diphenylamide | 30<br>10<br>10 | 0.15 | Graft | 1.2 | 32.0 |

<Notes of Table 1>
X-22-174BX: mass average molecular weight of 2,300
KF-2012: mass average molecular weight of 4,600
X-22-2426: mass average molecular weight of 12,000
(All trade names, manufactured by Shin-Etsu Chemical Co., Ltd., one-terminal methacrylic-modified silicone)
VPS-1001 (manufactured by Wako Pure Chemical Industries, Ltd., polysiloxane unit, mass average molecular weight of 10,000)

A formulation ratio is indicated by a mass ratio. In addition, amount of initiator (%)=addition amount of polymerization initiator/(addition amount of monomer for forming structural unit (a)+addition amount of monomer for forming structural unit (b))×100.

(Production of Resin Sheet 101)

The polymer 1 obtained above was used as a resin material, and this resin material was subjected to heat press treatment, and therefore a resin sheet 101 having a length of 60 mm, a width of 60 mm, and a thickness of 2 mm was prepared. The heat press treatment was carried out by filling a mold with the resin material and performing pressing at 10 MPa for 2 minutes with a pressing temperature set at 100° C. by using a "MINI TEST PRESS MP-WNL" manufactured by Toyo Seiki Co., Ltd.

(Production of Resin Sheets 102 to 128)

Resin sheets 102 to 128 were produced in the same manner as the resin sheet 101 using the polymers 2 to 21 obtained above as a resin material. In addition, because the pressing temperature was set to vary for each polymer, the heat press treatment was performed while adjusting the temperature.

(Production of Resin Sheet c11)

96 parts by mass of vinyl-terminated polydimethylsiloxane DMS-V41 (trade name, manufactured by GELEST, INC.), 4 parts by mass of a methylhydrosiloxane-dimethylsiloxane copolymer HMS-301 (trade name, manufactured by GELEST, INC.), and 0.03 parts by mass of a platinum catalyst SIP6830.3 (trade name, manufactured by GELEST, INC.) were mixed to be used as a resin material. This resin material was subjected to the heat press treatment and thermally cured at 150° C. for 5 minutes, and therefore a resin sheet c11 containing the polymer c1 and having a length of 60 mm, a width of 60 mm, and a thickness of 2 mm was produced.

(Production of Resin Sheet c12)

77 parts by mass of vinyl-terminated polydimethylsiloxane DMS-V41 (trade name, manufactured by GELEST, INC.), 3 parts by mass of a methylhydrosiloxane-dimethylsiloxane copolymer HMS-301 (trade name, manufactured by GELEST, INC.), 20 parts by mass of fumed silica AEROSIL R 974 (trade name, manufactured by NIPPON AEROSIL CO., LTD., average primary particle diameter of 12 nm, surface treated with dimethyldichlorosilane), and 0.05 parts by mass of a platinum catalyst SIP6830.3 (manufactured by GELEST, INC.) were mixed to be used as a resin material. This resin material was subjected to the heat press treatment and thermally cured at 150° C. for 5 minutes, and therefore a resin sheet c12 containing the polymer c2 and having a length of 60 mm, a width of 60 mm, and a thickness of 2 mm was produced.

(Production of Resin Sheet c13)

10 parts by mass of methyl methacrylate (manufactured by Wako Pure Chemical Industries, Ltd.), 90 parts by mass of bis(methacryloxypropyl)tetrakis(trimethylsiloxy)disiloxane (manufactured by Fluorochem Ltd.), and 0.5% by mass of 2,2'-azobis(isobutyronitrile) (AIBN, manufactured by Wako Pure Chemical Industries, Ltd.) were mixed, and 4.0% by mass of neopentyl glycol dimethacrylate was further added thereto. The mixed solution was heated in an oven at 60° C. for 12 hours and dried at 70° C. for 12 hours, and therefore a resin sheet having a length of 60 mm, a width of 60 mm, and a thickness of 2 mm was prepared.

[Density]

The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999).

In a case where the resin sheet does not contain components other than the polymer, the density measured by the above-described method corresponds to the density of the polymer.

<Evaluation of Ultrasonic Characteristics and Mechanical Strength>

The resin sheets 101 to 128 and c11 to c13 produced above were evaluated as follows. The obtained evaluation results are summarized in Table 2.

[Acoustic (Ultrasonic) Sensitivity]

A sinusoidal signal (a wave) of 10 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 10 MHz was generated in water from the ultrasound probe. The magnitude of the amplitude before and after the generated ultrasonic wave passed through each of the obtained resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.) The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet. As the acoustic (ultrasonic) sensitivity becomes high, the acoustic (ultrasonic) attenuation becomes low.

$$\text{Acoustic(ultrasonic)sensitivity} = 20 \times \text{Log}(Vs/Vin)$$

The acoustic (ultrasonic) sensitivity was evaluated according to the following evaluation standards. In this test, "C" or higher in the evaluation standard are acceptance levels.

(Evaluation Standard)

AA: −64 dB or more

A: −66 dB or more and less than −64 dB

B: −68 dB or more and less than −66 dB

C: −70 dB or more and less than −68 dB

D: less than −70 dB

[Acoustic Impedance]

The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured. The acoustic impedance was evaluated according to the following evaluation standards. In this test, "C" or higher in the evaluation standard are acceptance levels.

(Evaluation Standard)

AA: $1.30 \times 10^6$ kg/m$^2$/s or more

A: $1.25 \times 10^6$ kg/m$^2$/s or more and less than $1.30 \times 10^6$ kg/m$^2$/s B: $1.20 \times 10^6$ kg/m$^2$/s or more and less than $1.25 \times 10^6$ kg/m$^2$/s C: $1.10 \times 10^6$ kg/m$^2$/s or more and less than $1.20 \times 10^6$ kg/m$^2$/s D: less than $1.10 \times 10^6$ kg/m$^2$/s

[Hardness]

The type A durometer hardness of each of the obtained silicone resin sheets with a thickness of 2 mm was measured using a rubber hardness meter (trade name "RH-201A" manufactured by Excel co., Ltd.) in compliance with JIS K6253-3 (2012). "C" or higher in the evaluation standard are acceptance levels.

(Evaluation Standard)

AA: 50 degrees or more

A: 40 degrees or more and less than 50 degrees

B: 30 degrees or more and less than 40 degrees

C: 20 degrees or more and less than 30 degrees

D: 10 degrees or more and less than 20 degrees

E: 5 degrees or more and less than 10 degrees

F: less than 5 degrees

TABLE 3

| Resin sheet No. | Polymer | Additive | Density (g/cm$^3$) | Acoustic sensitivity | Acoustic impedance | Mechanical strength Hardness | Note |
|---|---|---|---|---|---|---|---|
| 101 | 1 | None | 1.00 | C | C | C | Example |
| 102 | 2 | None | 1.00 | B | C | B | Example |
| 103 | 3 | None | 1.00 | C | C | C | Example |
| 104 | 4 | None | 1.00 | B | C | B | Example |
| 105 | 5 | None | 1.00 | A | C | B | Example |
| 106 | 6 | None | 1.00 | A | C | A | Example |
| 107 | 7 | None | 1.00 | A | C | A | Example |
| 108 | 8 | None | 1.00 | B | C | A | Example |
| 109 | 9 | None | 1.00 | B | C | A | Example |
| 110 | 10 | None | 1.08 | B | A | A | Example |
| 111 | 11 | None | 1.08 | AA | B | A | Example |
| 112 | 12 | None | 1.10 | AA | A | A | Example |
| 113 | 13 | None | 1.11 | AA | A | A | Example |
| 114 | 14 | None | 1.10 | A | A | A | Example |
| 115 | 15 | None | 1.09 | A | B | A | Example |
| 116 | 16 | None | 1.12 | A | A | A | Example |
| 117 | 17 | None | 1.14 | A | A | A | Example |
| 118 | 18 | None | 1.12 | A | AA | A | Example |
| 119 | 19 | None | 1.09 | A | B | A | Example |
| 120 | 20 | None | 1.12 | A | AA | AA | Example |
| 121 | 21 | None | 1.12 | AA | AA | AA | Example |
| 122 | 22 | None | 1.13 | A | AA | AA | Example |
| 123 | 23 | None | 1.16 | A | A | AA | Example |
| 124 | 24 | None | 1.16 | A | A | AA | Example |
| 125 | 25 | None | 1.16 | A | A | AA | Example |
| 126 | 26 | None | 1.18 | AA | AA | AA | Example |

TABLE 3-continued

| Resin sheet No. | Polymer | Additive | Density (g/cm³) | Acoustic sensitivity | Acoustic impedance | Mechanical strength Hardness | Note |
|---|---|---|---|---|---|---|---|
| 127 | 27 | None | 1.18 | AA | AA | AA | Example |
| 128 | 28 | None | 1.18 | A | AA | AA | Example |
| c11 | c1 | None | 0.98 | A | D | F | Comparative Example |
| c12 | c2 | Silica | 1.08 | D | B | B | Comparative Example |
| c13 | c3 | None | 1.00 | D | AA | AA | Comparative Example |

As can be clearly seen from Table 2, the resin sheet of No. c11 formed of the polymer c1 that does not satisfy the requirement of the present invention was failed in the acoustic sensitivity and the mechanical strength. In addition, the resin sheet of No. c12 formed of the polymer c2 that does not satisfy the requirement of the present invention was failed in the acoustic sensitivity. Furthermore, the resin sheet of No. c13 formed of the polymer c3 that does not satisfy the requirement of the present invention, which is disclosed in JP1996-010344A (JP-H08-010344A), was failed in the acoustic sensitivity.

On the contrary, all of the resin sheets of Nos. 101 to 128 formed of the polymer that satisfies the requirement of the present invention, were excellent in the acoustic sensitivity, the acoustic impedance, and the mechanical strength.

As the acoustic characteristics of the resin sheet of No. 121, the damping coefficient at a frequency of 15 MHz was 0.40 dB/(MHz·mm), the acoustic impedance was $1.30 \times 10^6$ kg/m²/s, and the acoustic velocity was 1160 m/s. Images obtained in a case where the resin sheet of No. 121 was molded into the lens and attached to the ultrasound probe, were favorable.

[Damping Coefficient]

According to "method for measuring damping coefficient by pulse wave" of JIS Z 2354, the damping coefficient was measured from an amplitude spectrum obtained for each frequency by performing Fourier transform on echo signals passed through the sample.

The present invention has been described using an embodiment thereof. However, it is considered that, unless otherwise specified, even the detailed description of the invention is not limited and is necessarily widely interpreted without departing from the gist and the range of the invention shown in the attached Claims.

EXPLANATION OF REFERENCES

1: acoustic lens
2: acoustic matching layer
3: piezoelectric element layer
4: backing material
7: housing
9: cord
10: ultrasound probe (probe)

What is claimed is:

1. A method of forming a member constituting an acoustic wave probe, comprising:
molding a resin material containing a polymer that is formed of a structural unit (a) having a polysiloxane bond represented by Formula (1) and at least one of a structural unit (b) having a partial structure represented by Formula (2), wherein the structural unit (b) having the partial structure represented by Formula (2) is an acryloyloxy structural unit (b1), an acrylamide structural unit (b2), or a styrene structural unit (b3),

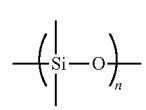

Formula (1)

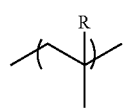

Formula (2)

in the formulas, n represents an integer of 3 or more, and R represents a hydrogen atom or a monovalent organic group; and a bond line extending downward from a carbon atom to which R bonds represents a bond; and a bond line extending from Si represents a bond.

2. The method of forming a member constituting an acoustic wave probe according to claim 1,
wherein the polymer is a graft polymer having the polysiloxane bond represented by Formula (1) at a side chain.

3. The method of forming a member constituting an acoustic wave probe according to claim 1,
wherein the structural unit having the polysiloxane bond represented by Formula (1) is represented by Formula (3), and
the acryloyloxy structural unit (b1) is represented by Formula (4), the acrylamide structural unit (b2) is represented by Formula (5), and the styrene structural unit (b3) is represented by Formula (6),

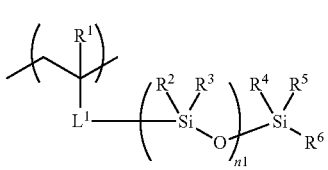

Formula (3)

in the formula, $R^1$ to $R^6$ each independently represent a hydrogen atom or a monovalent organic group, $L^1$ represents a divalent linking group, and n1 represents an integer of 3 to 10,000, Formula (4)

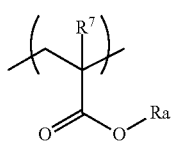

in the formula, $R^7$ and Ra each independently represent a hydrogen atom or a monovalent organic group, Formula (5)

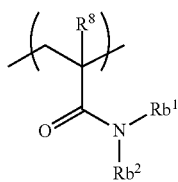

in the formula, $R^8$, $Rb^1$, and $Rb^2$ each independently represent a hydrogen atom or a monovalent organic group, and Formula (6)

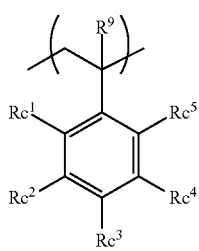

in the formula, $R^9$ and $Rc^1$ to $Rc^5$ each independently represent a hydrogen atom or a monovalent organic group.

4. The method of forming a member constituting an acoustic wave probe according to claim 1,
wherein the polymer is a block polymer having a block formed of the structural unit (a) having the polysiloxane bond represented by Formula (1) and at least one of a block formed of the structural unit (b) having the partial structure represented by Formula (2).

5. The method of forming a member constituting an acoustic wave probe according to claim 4,
wherein the structural unit (a) having the polysiloxane bond represented by Formula (1) is represented by Formula (7), and
the structural unit (b) having the partial structure represented by Formula (2) is represented by Formula (6), Formula (7)

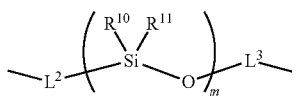

in the formula, $R^{10}$ and $R^{11}$ each independently represent a hydrogen atom or a monovalent organic group, $L^2$ and $L^3$ each independently represent a divalent linking group, and m represents an integer of 3 to 10,000, and Formula (6)

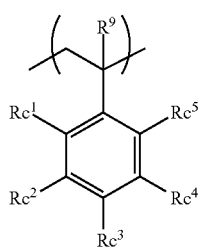

in the formula, $R^9$ and $Rc^1$ to $Rc^5$ each independently represent a hydrogen atom or a monovalent organic group.

6. The method of forming a member constituting an acoustic wave probe according to claim 4,
wherein the structural unit (a) having the polysiloxane bond represented by Formula (1) is represented by Formula (7), and
the structural unit (b) having the partial structure represented by Formula (2) is represented by Formula (4), Formula (7)

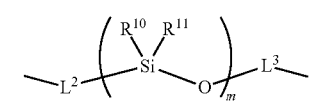

in the formula, $R^{10}$ and $R^{11}$ each independently represent a hydrogen atom or a monovalent organic group, $L^2$ and $L^3$ each independently represent a divalent linking group, and m represents an integer of 3 to 10,000, and Formula (4)

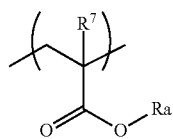

in the formula, $R^7$ and Ra each independently represent a hydrogen atom or a monovalent organic group.

7. The method of forming a member constituting an acoustic wave probe according to claim 1,
wherein, in the polymer, a mass average molecular weight of the structural unit having the polysiloxane bond represented by Formula (1) is 4,000 or more.

8. The method of forming a member constituting an acoustic wave probe according to claim 1,
wherein the structural unit (b) having the partial structure represented by Formula (2) is the styrene structural unit (b3).

9. The method of forming a member constituting an acoustic wave probe according to claim 1,
wherein the structural unit (b) having the partial structure represented by Formula (2) is the acryloyloxy structural unit (b1).

10. The method of forming a member constituting an acoustic wave probe according to claim 1,
wherein a density of the polymer is 1.05 g/cm$^3$ or more.

11. The method of forming a member constituting an acoustic wave probe according to claim 1,
wherein the polymer contains a fluorine atom.

12. The method of forming a member constituting an acoustic wave probe according to claim 11,
wherein the structural unit (b) having the partial structure represented by Formula (2) has 5 or more fluorine atoms.

13. The method of forming a member constituting an acoustic wave probe according to claim 1,
wherein a mass average molecular weight of the polymer is 50,000 or more.

14. An acoustic lens comprising a resin material for an acoustic wave probe, the resin material containing a polymer that is formed of a structural unit (a) having a polysiloxane bond represented by Formula (1) and at least one of a structural unit (b) having a partial structure represented by Formula (2),
wherein the structural unit (b) having the partial structure represented by Formula (2) is an acryloyloxy structural unit (b1), an acrylamide structural unit (b2), or a styrene structural unit (b3),

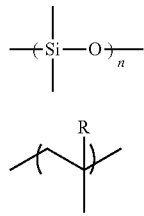

Formula (1)

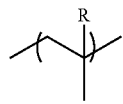

Formula (2)

in the formulas, n represents an integer of 3 or more, and R represents a hydrogen atom or a monovalent organic group; a bond line extending downward from a carbon atom to which R bonds represents a bond; and a bond line extending from Si represents a bond.

15. The acoustic lens according to claim 14, having a damping coefficient of 0.50 dB/(MHz·mm) or less at a frequency of 15 MHz, an acoustic impedance of $1.30 \times 10^6$ kg/m²/s or more and $1.70 \times 10^6$ kg/m²/s or less, and an acoustic velocity of 1300 m/s or less.

16. An acoustic wave probe comprising the acoustic lens according to claim 14.

17. An acoustic wave measurement apparatus comprising the acoustic wave probe according to claim 16.

18. An ultrasound diagnostic apparatus comprising the acoustic wave probe according to claim 16.

19. A photoacoustic wave measurement apparatus comprising the acoustic lens according to claim 14.

20. An ultrasound endoscope comprising the acoustic lens according to claim 14.

21. The method of forming a member constituting an acoustic wave probe according to claim 1, wherein the member constituting the acoustic wave probe is an acoustic lens or an acoustic matching layer.

\* \* \* \* \*